US009877937B2

(12) United States Patent
Hammer et al.

(10) Patent No.: US 9,877,937 B2
(45) Date of Patent: *Jan. 30, 2018

(54) COMPOUNDS AND METHODS FOR TREATING ABERRANT ADRENOCORTICAL CELL DISORDERS

(71) Applicants: Millendo Therapeutics, Inc., Ann Arbor, MI (US); The Regents of the University of Michigan, Ann Arbor, MI (US)

(72) Inventors: Gary Hammer, Ann Arbor, MI (US); Tom Kerppola, Ann Arbor, MI (US); Raili Kerppola, Ann Arbor, MI (US)

(73) Assignees: The Regents of the Univeristy of Michigan, Ann Arbor, MI (US); Millendo Therapeutics, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/170,682

(22) Filed: Jun. 1, 2016

(65) Prior Publication Data
US 2016/0367507 A1 Dec. 22, 2016

Related U.S. Application Data

(63) Continuation of application No. 14/798,237, filed on Jul. 13, 2015, now Pat. No. 9,446,010, which is a (Continued)

(51) Int. Cl.
*A61K 31/17* (2006.01)
*A61K 31/03* (2006.01)
(Continued)

(52) U.S. Cl.
CPC ............ *A61K 31/17* (2013.01); *A61K 9/0053* (2013.01); *A61K 31/03* (2013.01); *A61K 31/155* (2013.01);
(Continued)

(58) Field of Classification Search
None
See application file for complete search history.

(56) References Cited

U.S. PATENT DOCUMENTS 9,446,010 B2 * 9/2016 Hammer ................ A61K 31/17
2009/0192220 A1 7/2009 White et al.

FOREIGN PATENT DOCUMENTS

WO 2008/070692 A2 6/2008
WO 2009/067397 A2 5/2009

OTHER PUBLICATIONS

New. Nonclassical 21-hydroxylase deficiency. The Journal of Clinical Endocrinology & Metabolism, 91(11): 4205-4214, 2006.*
(Continued)

*Primary Examiner* — Anna Pagonakis
(74) *Attorney, Agent, or Firm* — Seed IP Law Group LLP

(57) ABSTRACT

Methods and compositions are provided for treatment of disorders associated with aberrant adrenal cortex cell behavior, including (but not limited to) treatment of adrenocortical carcinoma (ACC), Cushing's syndrome and/or pituitary ACTH excess (Cushing's Disease). Such methods involve administration of an effective amount N-(2,6-bis(1-methylethyl)phenyl)-N'-((1-(4-(dimethyl amino)phenyl)cyclopentyl)-methyl)urea hydrochloride to the patient.

1 Claim, 24 Drawing Sheets

Related U.S. Application Data continuation of application No. 13/802,047, filed on Mar. 13, 2013, now Pat. No. 9,107,883.

(60) Provisional application No. 61/614,269, filed on Mar. 22, 2012.

(51) Int. Cl.

| | | |
|---|---|---|
| *A61K 31/155* | (2006.01) | |
| *A61K 31/436* | (2006.01) | |
| *A61K 45/06* | (2006.01) | |
| *A61K 31/568* | (2006.01) | |
| *A61K 31/567* | (2006.01) | |
| *A61K 31/573* | (2006.01) | |
| *A61K 31/58* | (2006.01) | |
| *A61K 9/00* | (2006.01) | |

(52) U.S. Cl.
CPC .......... *A61K 31/436* (2013.01); *A61K 31/567* (2013.01); *A61K 31/568* (2013.01); *A61K 31/573* (2013.01); *A61K 31/58* (2013.01); *A61K 45/06* (2013.01)

(56) References Cited

OTHER PUBLICATIONS

Miller. Genetics, Diagnosis, and Management of 21-hydroxylase Deficiency. Journal of Clinical Endocrinology and Metabolism. vol. 78, No. 2, 1994.*
Beauregard et al., "Classic and Recent Etiologies of Cushing's Syndrome," *Treat. Endocrinol.*, 1 (2): 79-94 (2002).
Villa et al., "Modulation of cytotoxic drug activity by mitotane and Ionidamine in human adrenocortical carcinoma cells," *International Journal of Oncology*, 14(1): 133-138 (1999).
Chen et al., "Treatment of Adrenocortical Carcinoma: Contemporary Outcomes," *Current Urology Reports*, 5(1): 65-72, Feb. 1, 2004.
Dominick et al., "Morphogenesis of a Zone-Specific Adrenocortical Cytotoxicity in Guinea Pigs Administered PD 132301-2, an Inhibitor of Acyl-CoA: Cholesterol Acyltransferase," *Toxicology Pathology* 21(1):54-62, 1993.
Dominick et al., "Subacute Toxicity of a Novel Inhibitor of Acyl-CoA:Cholesterol Acyltransferase in Beagle Dogs," *Fundamental and Applied Toxicology* 20: 217-224, 1993.
Harvey et al., "Adrenal Toxicology: Molecular Targets, Endocrine Mechanisms, Hormonal Interactions, Assessment Models, and Species Differences in Toxicity," Chapter 1 in *Introduction to Adrenal Toxicology*, Harvey et al., eds., ISBN: 978140061291, Oct. 2008, downloaded from informahealthcare.com on Nov. 15, 2012.
Junquero et al., "Pharmacological profile of F 12511, (S)-2',3',5'-trimethyl-4'-hydroxy-α-dodecylthioacetanilide a powerful and systemic acylcoenzyme A:cholesterol acyltransferase inhibitor," *Biochemical Pharmacology* 61: 97-108, 2001.
Krause et al., "Divergent Pharmacologic Activitites of PD 132301-2 and CL 277,082, Urea Inhibitors of Acyl-CoA: Cholesterol Acyltransferase," *The Journal of Pharmacology and Experimental Therapeutics* 267(2): 734-743, 1993.
Krone et al., "Gas chromatography/mass spectrometry (GC/MS) remains a pre-eminent discovery tool in clinical steroid investigations even in the era of fast liquid chromatography tandem mass spectrometry (LC/MS/MS)," *Journal of Steroid Biochemistry & Molecular Biology*, vol. 121, pp. 496-504 (2010).

Leon et al., "Potential Role of Acyl-Coenzyme A: Cholesterol Transferase (ACAT) Inhibitors as Hypolipidemic and Antiatherosclerosis Drugs," *Pharmaceutical Research* 22(10): 1578-1588, Oct. 2005.
Matsuo et al., "Difference between Normal and WHHL Rabbits in Susceptibility to the Adrenal Toxicity of an Acyl-CoA:Cholesterol Acyltransferase Inhibitor, FR145237," *Toxicology and Applied Pharmacology* 140: 387-392, 1996.
Nishimura et al., "Effects of compound X, a novel potent inhibitor of acyl-coenzyme A:cholesterol O-acyltransferase, on the adrenal gland of rats," *Exp Toxicol Pathol* 65: 961-971, Nov. 2013.
Merke et al., "Congenital adrenal hyperplasia," *Lancet*, 365: 2125-2136, Jun. 18, 2005.
Purchase et al., "Inhibitors of Acyl-CoA:Cholesterol Acyltransferase: Novel Trisbustituted Ureas as Hypocholesterolemic Agents," *Bioorganic & Medicinal Chemistry* 5(4): 739-747, 1997.
Reindel et al., "Comparative Adrenotoxicity of a Novel ACYL-COA:Cholesterol Acyltransferase (ACT) Inhibitor (PD132301-2) in Laboratory Animals," *Toxicol Pathol* 20: A642, 1992 [Abstract only, one page].
Reindel et al., "Toxicologic Effects of a Novel Acyl-CoA : Cholesterol Acyltransferase Inhibitor in Cynomolgus Monkeys," *Toxicologic Pathology* 22(5): 510-518, 1994.
Ribelin, "The Effects of Drugs and Chemicals upon the Structure of the Adrenal Gland," *Fundamental and Applied Toxicology* 4: 105-119, 1984.
Rosol et al., "Adrenal Gland: Structure, Function, and Mechanisms of Toxicity," *Toxicologic Pathology* 29(1): 41-48, 2001.
Saxena et al., "Acyl-coenzyme A:cholesterol-acyltransferase (ACAT) inhibitors modulate monocyte adhesion to aortic endothelial cells," *Atherosclerosis* 112: 7-17, 1995.
Sliskovic and Trevedi, "ACAT Inhibitors: Potential Anti-atherosclerotic Agents," *Current Medicinal Chemistry* 1: 204-225, 1994.
Sliskovic et al., "α-Substituted Malonester Amides: Tools to Define the Relationship between ACAT Inhibition and Adrenal Toxicity," *J Med Chem* 41(5): 682-690, 1998.
Sliskovic et al., "3 ACAT Inhibitors: The Search for a Novel and Effective Treatment of Hypercholesterolemia and Atherosclerosis," *Progress in Medicinal Chemistry* 39: 121-171, 2002.
Trivedi et al., "Inhibitors of Acyl-CoA:Cholesterol Acyltransferase (ACAT). 7. Development of a Series of Substituted N-Phenyl-N'-[1-phenylcyclopentyl)methyl]ureas with Enhanced Hypocholesterolemic Activity," *J Med Chem* 37(11): 1652-1659, 1994.
Trivedi et al., "A Series of Conformationally and Sterically Constrained Analogs of N-phenyl-N'-aralkylurea ACAT Inhibitors," *Bioorganic & Medicinal Chemistry Letters* 5(19): 2229-2234, 1995.
Vernetti et al., "ATP Depletion is Associated with Cytotoxicity of a Novel Lipid Regulator in Guinea Pig Adrenocortical Cells," *Toxicology and Applied Pharmacology* 118: 30-38, 1993.
Vernetti et al., "Differential Toxicity of an Inhibitor of Mitochondrial Respiration in Canine Hepatocytes and Adrenocortical Cell Cultures," *Toxicology in Vitro* 10: 51-57, 1996.
Wolfgang et al., "Isolation and Use of Primary Adrenocortical Cells from Guinea Pigs, Dogs and Monkeys for In Vitro Toxicity Studies," *Toxicology Methods* 4(3):149-160, 1994.
Wolfgang et al., "Biochemical Alterations in Guinea Pig Adrenal Cortex Following Administration of PD 132301-2, an Inhibitor of Acyl-CoA:Cholesterol Acyltransferase," *Life Sciences* 56(13): 1089-1093, 1995.
Wolfgang et al., "Hepatic and Adrenal Toxicity of a Novel Lipid Regulator in Beagle Dogs," *Fundemantal and Applied Toxicology* 26: 272-281, 1995.

* cited by examiner

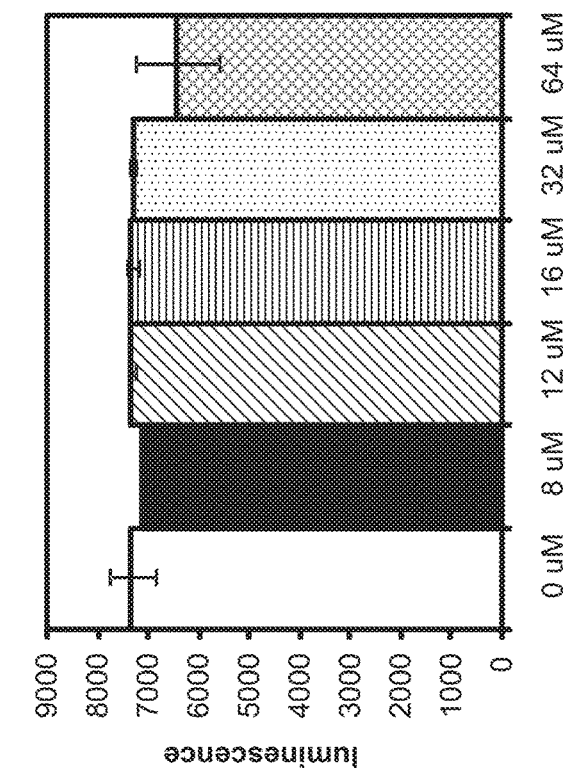
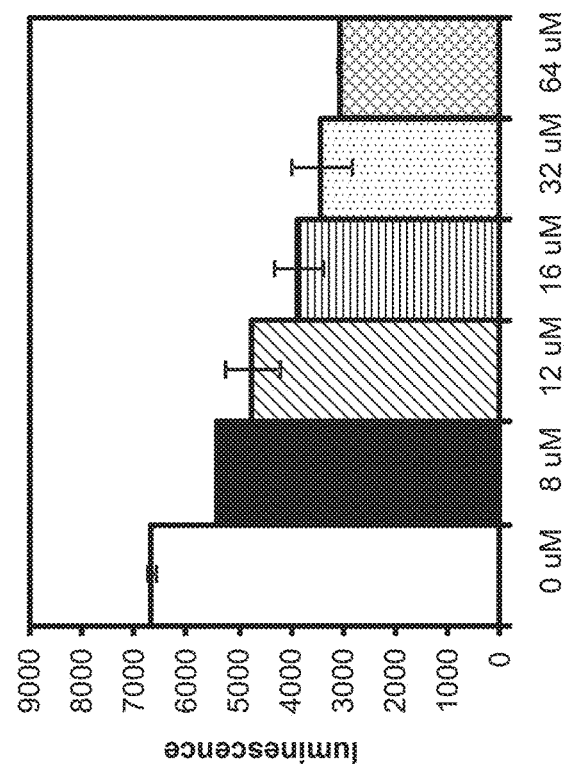
Fig. 12A
Fig. 12B

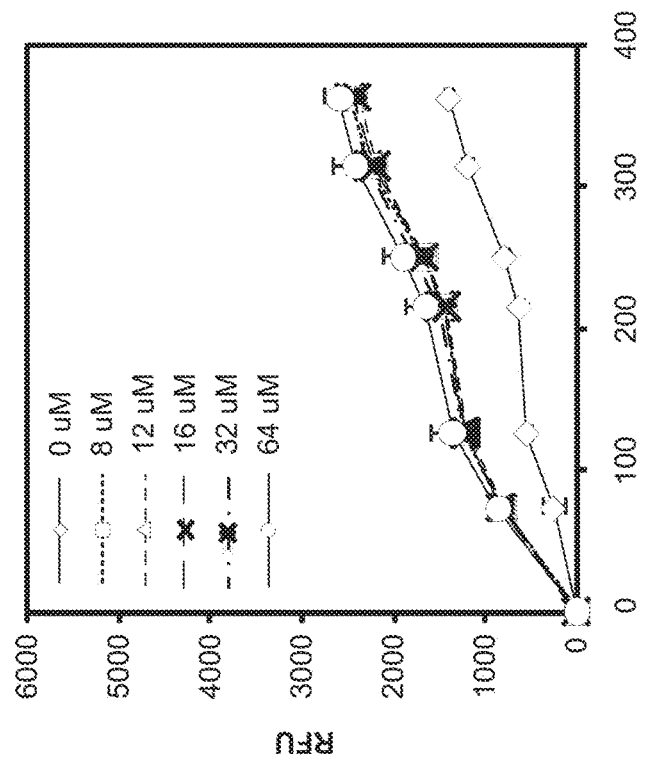
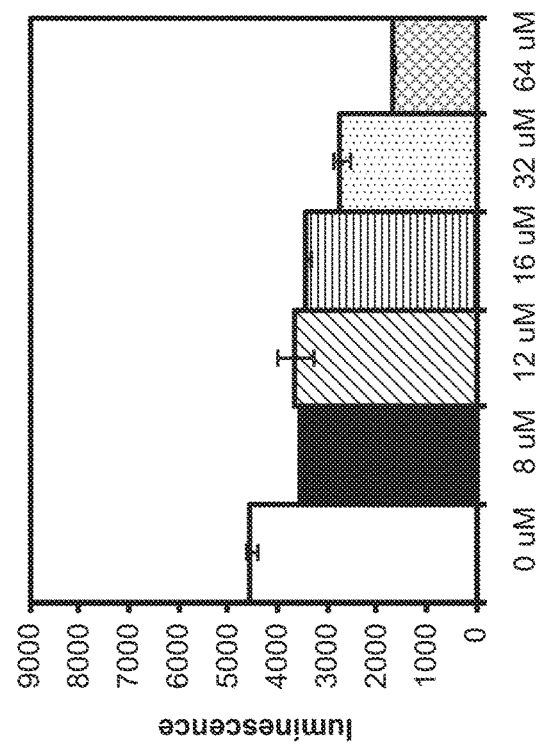
Fig. 12C
Fig. 12D

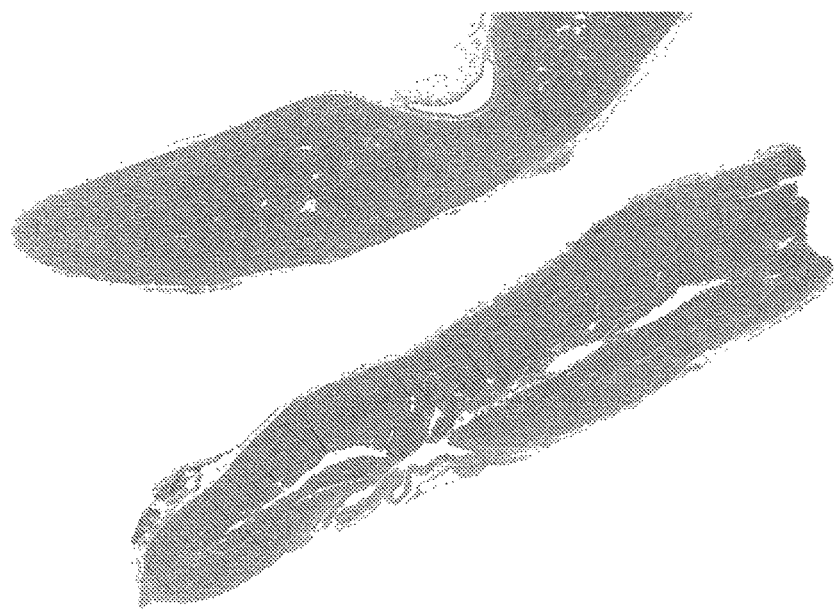
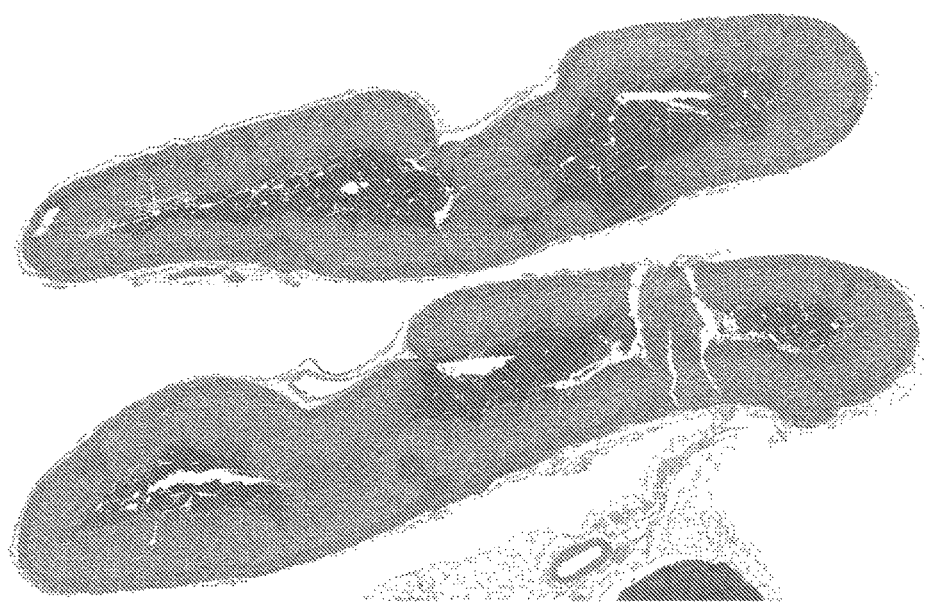

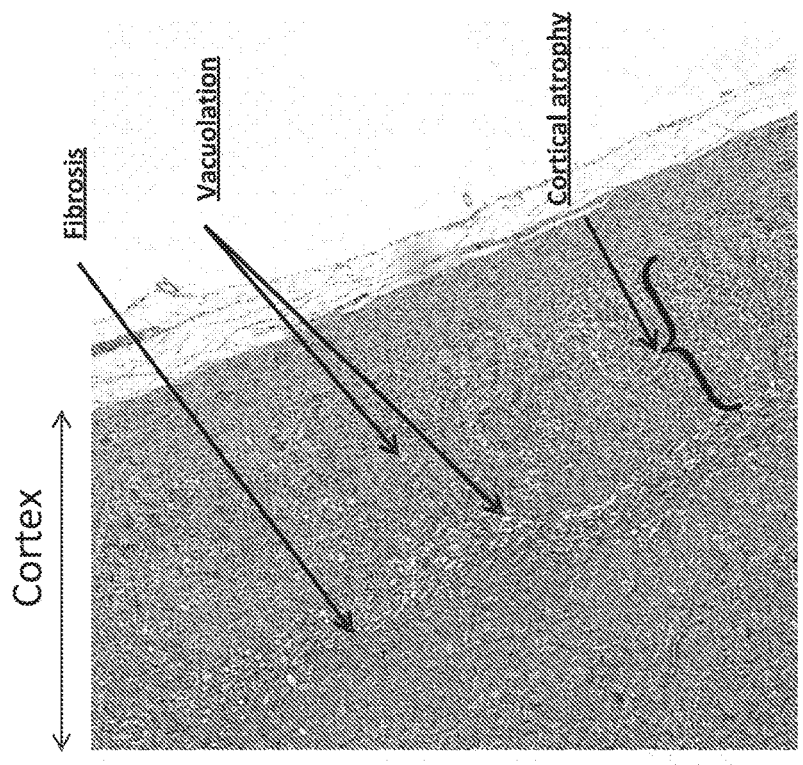
Fig. 15D ATR-101 (30 mpk)
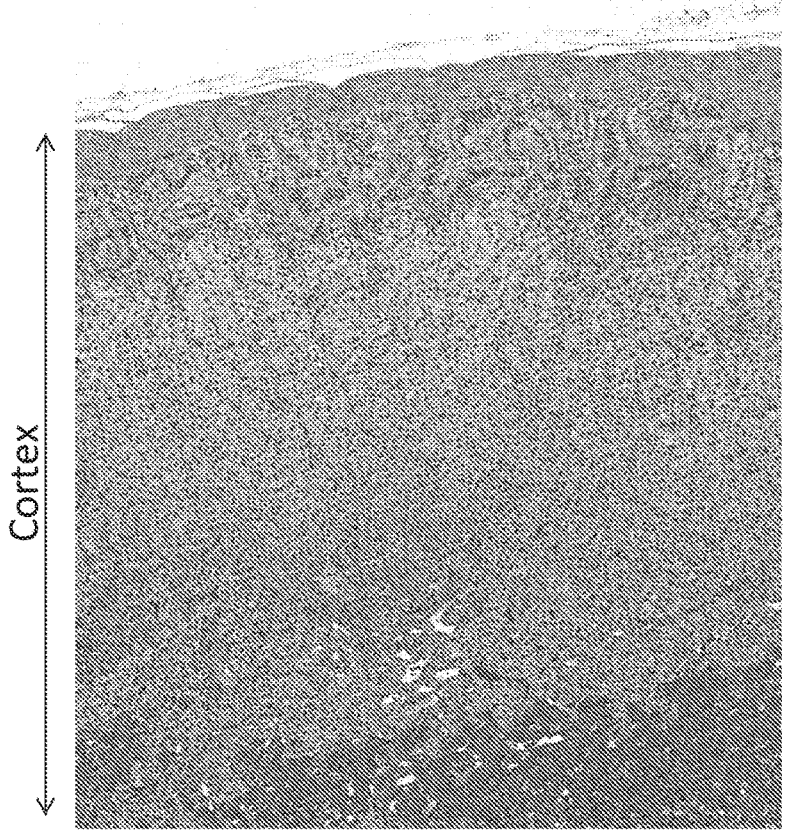
Fig. 15C Control

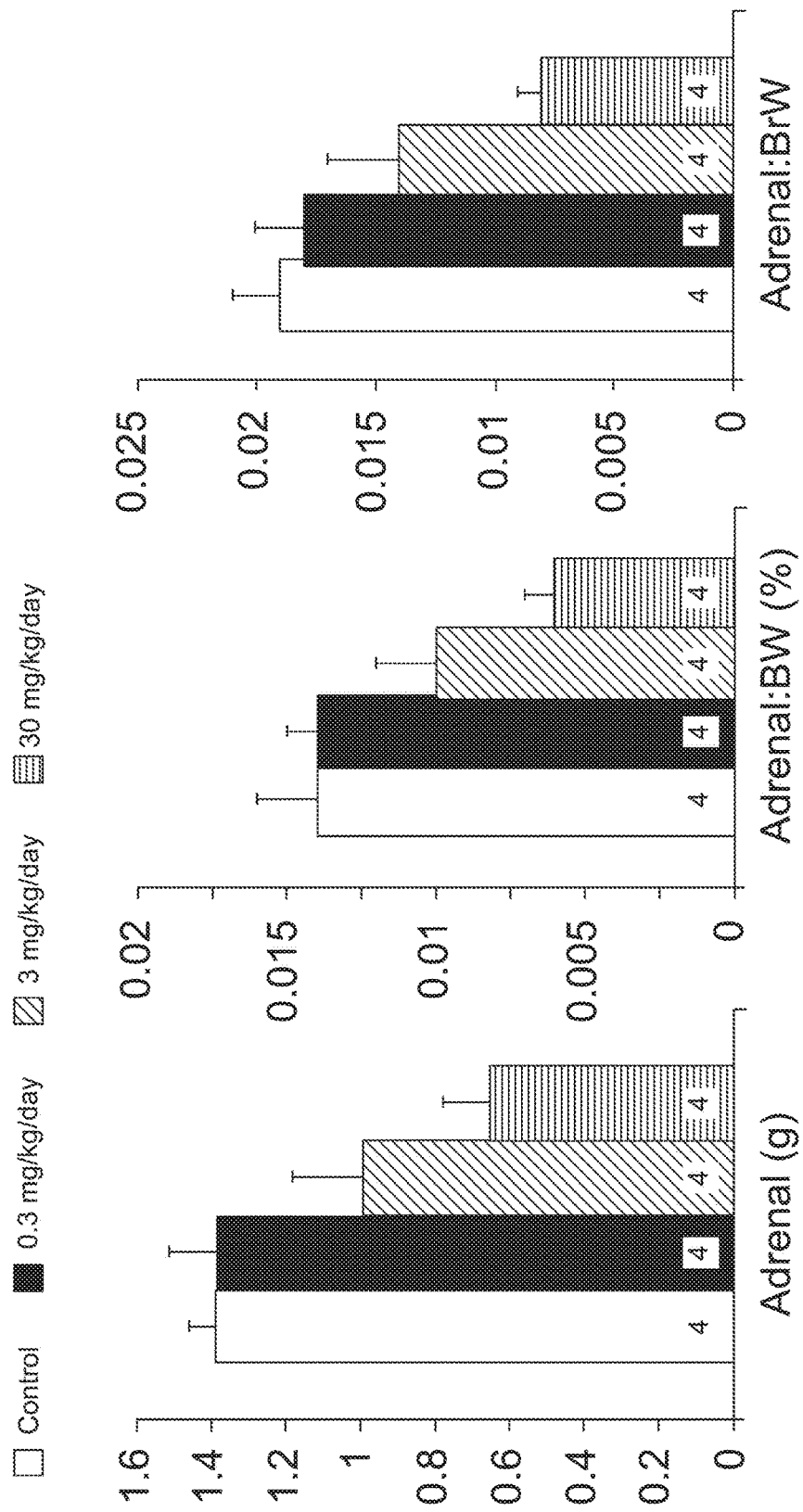

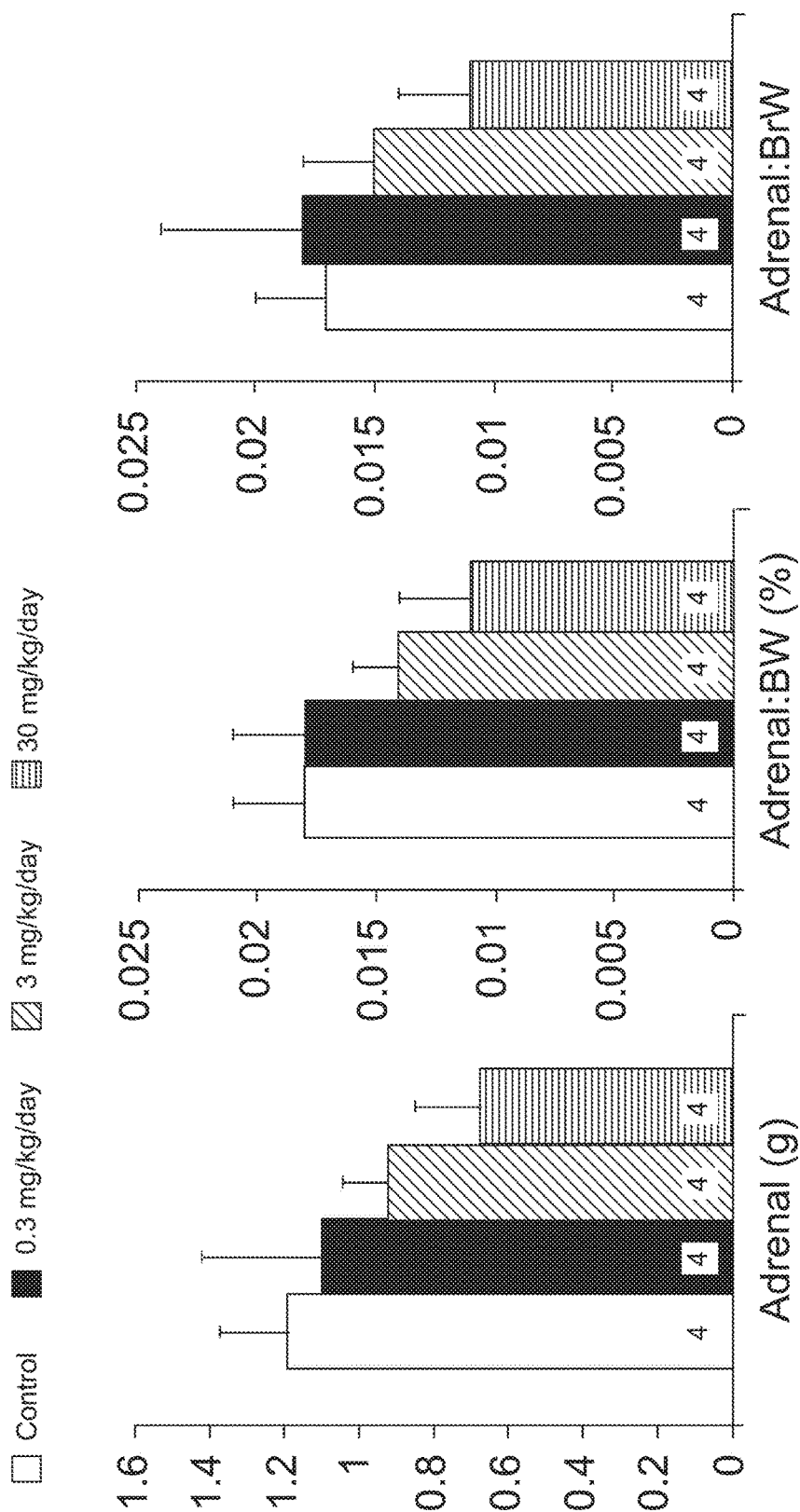

COMPOUNDS AND METHODS FOR TREATING ABERRANT ADRENOCORTICAL CELL DISORDERS

CROSS REFERENCE TO RELATED APPLICATION

This application claims the benefit under 35 U.S.C. § 119(e) to U.S. Provisional Application No. 61/614,269 filed on Mar. 22, 2012, which application is incorporated by reference herein in its entirety.

STATEMENT OF GOVERNMENT INTEREST

This invention was made with government support under grants DA030339 and GM086213 awarded by the National Institutes of Health. The government has certain rights in the invention.

BACKGROUND

Technical Field

Methods and compositions are provided for treatment of disorders associated with aberrant adrenal cortex cell behavior.

Description of the Related Art

The adrenal gland is made up of two parts: the outer cortex in which certain hormones are produced, and the inner medulla which is part of the nervous system, wherein nervous system hormones are produced. The cortex is devoted to the synthesis of corticosteroid and androgen hormones. Specific cortical cells produce particular hormones including aldosterone, cortisol, and androgens such as androstenedione. Adrenocortical tumors originate in the cortex.

There are two main types of adrenal cortex tumors: adenomas which are benign and adrenocortical carcinoma which are malignant. Adenomas in many people produce no symptoms, but in some instances the tumors lead to excess hormones production. Adrenocortical carcinoma can produce the hormones cortisol, aldosterone, estrogen, or testosterone, as well as other hormones. Adrenocortical carcinomas (ACC) are rare, highly malignant tumors. In women the tumor often releases these hormones, which can lead to male characteristics. The excess hormones may or may not cause symptoms. In general, adenomas are treated by removal of the adrenal gland or with therapeutic intervention. Likewise, adrenocortical carcinomas can lead to hormone production that can cause noticeable body changes such as weight gain, fluid build-up, early puberty in children, or excess facial or body hair in women. While the cause is unknown, adrenocortical carcinoma is most common in children younger than 5 and adults in their 30s and 40s. Adrenocortical carcinoma may be linked to a cancer syndrome that is passed down through families (inherited). Both men and women can develop this tumor.

Various stages of adrenocortical carcinomas are defined as follows. Stage I is cancer of the adrenal gland that is smaller than 5 centimeters (smaller than 2 inches) and is found in the adrenal gland only. Stage II is cancer of the adrenal gland that is larger than 5 centimeters (about 2 inches) and is found in the adrenal gland only. Stage III is cancer of the adrenal gland that has spread into fat and lymph nodes near the adrenal gland. Stage IV is cancer of the adrenal gland that has spread to fat or organs and to lymph nodes near the adrenal gland or to other parts of the body, such as lungs, liver, bones, and abdomen.

While the understanding of the disease has advanced with the advent of modern molecular techniques, the prognosis of patients with advanced disease, who represent about half of the diagnoses, remains dismal. Targeted therapies are in clinical development, but whether they will yield breakthroughs in the management of the disease is yet unknown (Hammer, G. D. and T. Else, eds., *Adrenocortical Carcinoma, Basic Science and Clinical Concepts*, 2011, New York: Springer).

The sole FDA-approved therapeutic agent for ACC is mitotane (o.p'-DDD), a derivative of the insecticide DDT, discovered in 1950s, when it was found to destroy the adrenal cortex of dogs. Despite half a century of use, its molecular mechanism remains unclear. The drug requires chemical transformation into an active, free radical form, which then induces lipid peroxidation and cell death. Mitotane also suppresses steroidogenesis and inhibits other cytochrome P450-class enzymes (Id.).

Whereas mitotane is widely used for the treatment of ACC, it has increased progression-free survival in only one-quarter to one-third of patients. For the patients that derive a therapeutic benefit, the effect is transient, delaying disease progression by an average of five months (Id.). Mitotane has numerous problems as a therapeutic agent, making its use difficult, and requiring close monitoring of patients. These problems include:

Severe side effects: practically all patients experience gastrointestinal dysfunctions and CNS symptoms. Mitotane causes elevated cholesterol and triglycerides, lowered thyroid hormone function, elevated liver enzymes, and leukopenia (Id.);

Narrow therapeutic window: 14 mg/l is required for therapeutic benefit, 20 mg/l is toxic (Hermsen, I. G., et al., *J. Clin. Endocrinol. Metab.*, 96(6):1844-51, 2011); and Poor ADME properties: The dose of mitotane must be frequently adjusted to achieve an adequate rate of loading without causing side effects. Even with a high drug intake by patients, it takes several months to reach target therapeutic blood levels. The drug accumulates in fat tissue, with an elimination half-life of months. Mitotane interferes with the metabolism of other drugs, making medical management of the many debilitating symptoms and additional chemotherapy of ACC patients challenging (Kroiss, M., et al., *Clin. Endocrinol.* (Oxf) 75(5):585-91, 2011; van Erp, N. P, *Eur. J. Endocrinol.* 164(4):621-6, 2011).

Because of the multiple limitations of mitotane as a therapy for ACC, a replacement with better efficacy and safety profile is highly desirable for the management of this deadly disease.

BRIEF SUMMARY

In brief, methods are disclosed for treating various disorders or conditions by administering a therapeutically effective amount of N-(2,6-bis(1-methylethyl)phenyl)-N'-((1-(4-(dimethylamino)phenyl)cyclopentyl)-methyl)urea hydrochloride (ATR-101) to a patient, wherein such methods include treating adrenocortical carcinoma (ACC), benign adenoma, increased hormone production, metastatic adrenocortical carcinoma, congenital adrenal hyperplasia, Cushing's syndrome, excess cortisol production, symptoms associated with excess cortisol production, hyperaldosteronism or 21-hydroxylase deficiency, as well as reducing adrenocortical tumor size.

In one embodiment, a method is disclosed for treating ACC in a patient comprising administering a therapeutically effective amount of ATR-101 to the patient.

In another embodiment, a method is disclosed for treating Cushing's syndrome in a patient comprising administering a therapeutically effective amount of ATR-101 to the patient.

In another embodiment, the above methods further comprise administering a second therapeutic agent. In a further embodiment, a second therapeutic agent is a chemotherapeutic agent, mitotane, mifepristone, metformin, everolimus, a targeting agent, an adrenolysis agent, or an IGFR antagonist.

In another embodiment, a method is disclosed for inhibiting aberrant adrenal hormone production in a patient comprising administering an effective amount of ATR-101 to the patient to inhibit hormone production. In a further embodiment, the method further comprises administering a second therapeutic agent. In yet a further embodiment, the hormone is a mineralocorticoid (including aldosterone), a glucocorticoid (including cortisol), or an androgen (including androstenedione, dehydroepiandrosterone, and adrenosterone).

In a further embodiment, the above methods comprise administering ATR-101 by oral administration.

In a further embodiment, the patient treated by the above methods is administered ATR-101 one, two, three, or four times daily.

In further embodiments, the patient treated by the above methods suffers from a condition selected from the group consisting of Cushing's syndrome; excess cortisol production; ACTH excess that results in adrenal cortisol excess; pituitary ACTH excess (Cushing's disease); ectopic ACTH syndrome; primary adrenal cortisol excess; or ACTH independent macronodular hyperplasia (always bilateral); or congenital adrenal hyperplasia (including 11 hydroxylase deficiency, 21-hydroxylase deficiency, hyperaldosteronism (Conn syndrome), or bilateral adrenal hyperplasia).

In another embodiment, a composition is disclosed comprising ATR-101 and a second therapeutic agent in a unit dose. In a further embodiment, the second therapeutic agent is a chemotherapeutic agent. In a further embodiment, the second therapeutic agent is selected from the group consisting of: mifepristone; a chemotherapeutic agent; metformin; everolimus; a targeting agent; an adrenolysis agent; and an IGFR antagonist.

BRIEF DESCRIPTION OF THE DRAWINGS

FIGS. 12A-F depicts the effects of cholesterol depletion on the changes in ATP levels caused by ATR-101 in H295R cells. The indicated concentrations of ATR-101 were added to H295R cells that were cultured 4 days in serum-free media followed by: (A) 4 hours with ATR-101; (B) 4 hours with ATR-101 and MβCD (2 mM); or (C) 4 hours with ATR-101 and MβCD (2 mM) complexed with cholesterol. The bars show the mean luminescence signals of lysates prepared after 4 hour incubation with ATR-101. The indicated concentrations of ATR-101 were added to H295R cells: (D) depicts the effect of ATR-101 on resazurin reduction in H295R cells; (E) depicts the effect of ATR-101 and MβCD (2 mM) on resazurin reduction in H295R cells; and (F) depicts the effect of ATR-101 and MβCD (2 mM) complexed with cholesterol on resazurin reduction in H295R cells.

FIGS. 15A-E depict the histopathology of adrenal glands of dogs administered high dose of ATR-101 vs. control animals.

FIGS. 16A-C depict adrenal weights in male dogs after administration of 0, 0.3, 3, or 30 mg/kg/day of ATR-101 for 28 days. FIG. 16A depicts the dose-related changes in absolute adrenal weight. FIG. 16B depicts the dose-related changes in adrenal-to-body weight ratio (Adrenal:BW (%)). FIG. 16C depicts the dose-related changes in adrenal-to-brain weight ratio (Adrenal:BrW).

FIGS. 17A-C depicts adrenal weights in female dogs after administration of 0, 0.3, 3, or 30 mg/kg/day of ATR-101 for 28 days. FIG. 17A depicts the dose-related changes in absolute adrenal weight. FIG. 17B depicts the dose-related changes in adrenal-to-body weight ratio (Adrenal:BW (%)). FIG. 17C depicts the dose-related changes in adrenal-to-brain weight ratio (Adrenal:BrW).

DETAILED DESCRIPTION

Definitions

Figure 1:
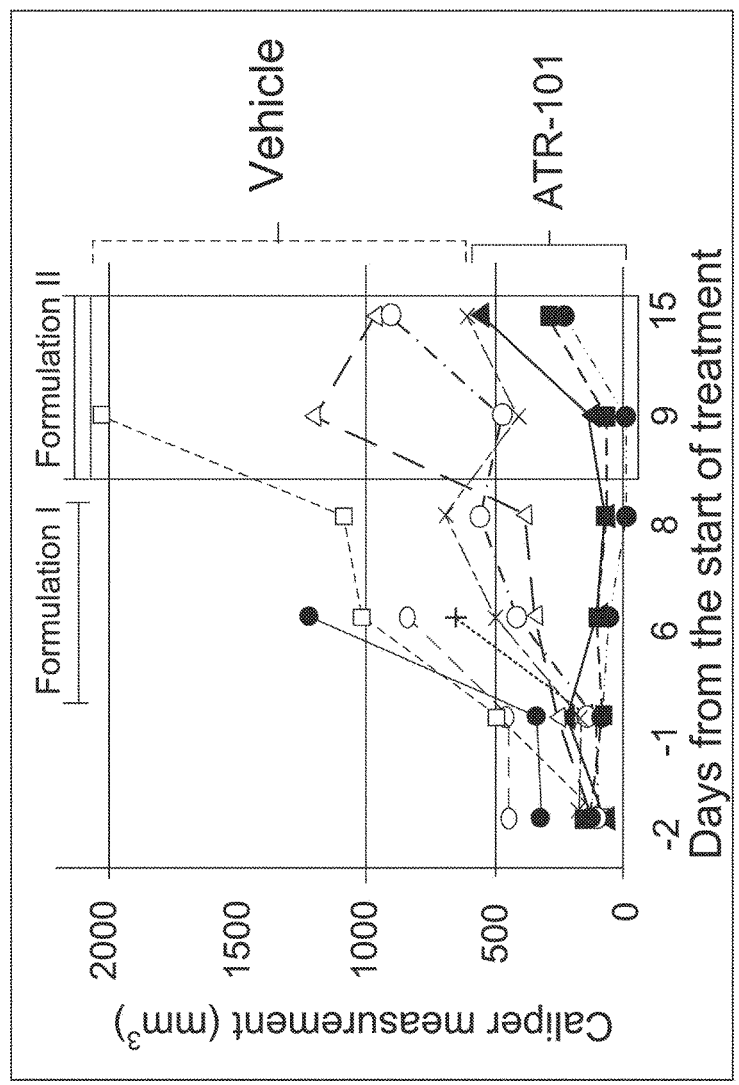
FIG. 1 depicts the effects of ATR-101 treatment on the sizes of H295R cell line xenotransplants in SCID mice. The solid lines with filled symbols represent mice administered 300 mg/kg/day ATR-101. The dashed lines and open symbols represent mice administered vehicle. During the first 8 days of administration, ATR-101 was administered in 10% DMSO, 0.9% NaCl, 0.5% CMC pH 3.9, 0.2% Tween-20 (Formulation I). Subsequently, ATR-101 was administered in 0.5% CMC pH 1.9, 0.2% Tween-20 (Formulation II).

As used herein, "treatment" includes therapeutic applications to slow or stop progression of a disorder associated with aberrant adrenocortical cellular activity, prophylactic application to prevent development of a disorder associated with aberrant adrenocortical cellular activity, and reversal of a disorder associated with aberrant adrenocortical cellular activity. Reversal of a disorder differs from a therapeutic application which slows or stops a disorder in that with a method of reversing, not only is progression of a disorder completely stopped, cellular behavior is moved to some degree, toward a normal state that would be observed in the absence of aberrant adrenocortical cellular activity.

As used herein, "aberrant adrenocortical cellular behavior" includes increased hormone production, benign adenoma, adrenocortical carcinoma, metastatic adrenocortical carcinoma, congenital adrenal hyperplasia, hyperaldosteronism including Conn syndrome, a unilateral aldosterone-producing adenoma, bilateral adrenal hyperplasia (or idiopathic hyperaldosteronism (IHA)), renin-responsive adenoma, primary adrenal hyperplasia and glucocorticoid-remediable aldosteronism (GRA), and 21-hydroxylase deficiency. Accordingly, "disorders associated with aberrant adrenocortical cellular activity" is used herein to mean symptoms and/or conditions that arise, either directly or indirectly, from aberrant adrenocortical cellular behavior. As will become apparent herein, these symptoms and/or conditions that arise from, either directly or indirectly, from aberrant adrenocortical cellular behavior are numerous. As used herein, "adrenocortical" and "adrenal cortex" are intended to mean the same.

As used herein, "Cushing's syndrome" means a hormonal disorder caused by prolonged exposure of the body's tissues to high levels of cortisol. Cushing's syndrome is sometimes referred to as "hypercortisolism" (excess cortisol production). Cushing's syndrome includes various subtypes of the disease, including Cushing's disease, adrenal Cushing's syndrome, and ectopic ACTH syndrome, which are categorized by the cause of hypercortisolism. Cushing's disease, also known as pituitary Cushing's, is caused by a pituitary gland tumor which secretes excessive ACTH, which in turn stimulates the adrenal glands to make more cortisol. Ectopic ACTH syndrome is caused by tumors that arise outside the pituitary gland that can produce ACTH, which stimulates cortisol production. Adrenal Cushing's syndrome is caused by an abnormality of the adrenal gland, usually an adrenal tumor, that causes excess cortisol secretion.

As used herein, the phrase "metastatic cancer" is defined as a cancer that has the potential to, or has begun to, spread to other areas of the body.

As used herein, the phrase term "therapeutically effective amount" refers to an amount of a therapeutic agent to treat, ameliorate, or prevent a disease or condition, or to exhibit a detectable therapeutic or preventative effect. The effect is detected by, for example, a reduction in tumor size. The effect is also detected by, for example, chemical markers or antigen levels. Therapeutic effects also include reduction in physical symptoms, such as decreased body temperature. The precise effective amount for a subject will depend upon the subject's size and health, the nature and extent of the condition, the therapeutics or combination of therapeutics selected for administration, and other variables known to those of skill in the art. The effective amount for a given situation is determined by routine experimentation and is within the judgment of the clinician.

A "prodrug" is a compound typically having little or no pharmacological activity itself but capable of releasing, for example by hydrolysis or metabolic cleaving of a linkage such as an ester moiety, an active drug upon administration to a subject.

Methods

Provided herein are methods for treatment of a disorder associated with aberrant adrenal cortex cellular activity. In various aspects, methods are also provided for slowing or stopping progression of a disorder associated with aberrant adrenal cortex cellular activity. In various aspects, methods are also provided for preventing a disorder associated with aberrant adrenal cortex cellular activity. In various aspects, methods are also provided for reversing a disorder associated with aberrant adrenal cortex cellular activity.

Methods according to the disclosure also include slowing or stopping progression, preventing or reversing a symptom associated with aberrant adrenal cortex cell behavior.

Treating

In various aspects, a method for treating increased hormone production in a patient is provided comprising administering a therapeutically effective amount of ATR-101 to the patient.

In various aspects, a method for treating benign adenoma in a patient is provided comprising administering a therapeutically effective amount of ATR-101 to the patient.

In various aspects, a method for treating adrenocortical carcinoma in a patient is provided comprising administering a therapeutically effective amount of ATR-101 to the patient.

In various aspects, a method for treating metastatic adrenocortical carcinoma in a patient is provided comprising administering a therapeutically effective amount of ATR-101 to the patient.

In various aspects, a method for treating congenital adrenal hyperplasia in a patient is provided comprising administering a therapeutically effective amount of ATR-101 to the patient.

In various aspects, a method for treating Cushing's syndrome in a patient is provided comprising administering a therapeutically effective amount of ATR-101 to the patient.

In various aspects, a method for treating excess cortisol production in a patient is provided comprising administering a therapeutically effective amount of ATR-101 to the patient.

In various aspects, a method for treating symptoms associated with excess cortisol production in a patient is provided comprising administering a therapeutically effective amount of ATR-101 to the patient.

In various aspects, a method for treating hyperaldosteronism in a patient is provided comprising administering a therapeutically effective amount of ATR-101 to the patient.

In various aspects, a method for treating Conn syndrome in a patient is provided comprising administering a therapeutically effective amount of ATR-101 to the patient.

In various aspects, a method for treating unilateral aldosterone-producing adenoma in a patient is provided comprising administering a therapeutically effective amount of ATR-101 to the patient.

In various aspects, a method for treating bilateral adrenal hyperplasia (or idiopathic hyperaldosteronism (IHA)) in a patient is provided comprising administering a therapeutically effective amount of ATR-101 to the patient.

In various aspects, a method for treating renin-responsive adenoma in a patient is provided comprising administering a therapeutically effective amount of ATR-101 to the patient.

In various aspects, a method for treating primary adrenal hyperplasia in a patient is provided comprising administering a therapeutically effective amount of ATR-101 to the patient.

In various aspects, a method for treating glucocorticoid-remediable aldosteronism (GRA) in a patient is provided comprising administering a therapeutically effective amount of ATR-101 to the patient.

In various aspects, a method for treating 21-hydroxylase deficiency in a patient is provided comprising administering a therapeutically effective amount of ATR-101 to the patient.

In various aspects, a method for reducing adrenocortical tumor size in a patient is provided comprising administering an effective amount of ATR-101 to the patient.

In various aspects, a method of inhibiting aberrant adrenal hormone production in a patient is provided comprising administering an effective amount of ATR-101 to the patient to inhibit hormone production.

Slowing or Stopping Progression

In various aspects, a method for slowing or stopping progression of increased hormone production in a patient is provided comprising administering a therapeutically effective amount of ATR-101 to the patient.

In various aspects, a method for slowing or stopping progression of benign adenoma in a patient is provided comprising administering a therapeutically effective amount of ATR-101 to the patient.

In various aspects, a method for slowing or stopping progression of adrenocortical carcinoma in a patient is provided comprising administering a therapeutically effective amount of ATR-101 to the patient.

In various aspects, a method for slowing or stopping progression of metastatic adrenocortical carcinoma in a patient is provided comprising administering a therapeutically effective amount of ATR-101 to the patient.

In various aspects, a method for slowing or stopping progression of Cushing's syndrome in a patient is provided comprising administering a therapeutically effective amount of ATR-101 to the patient.

In various aspects, a method for slowing or stopping progression excess cortisol production in a patient is provided comprising administering a therapeutically effective amount of ATR-101 to the patient.

In various aspects, a method for slowing or stopping progression of symptoms associated with excess cortisol production in a patient is provided comprising administering a therapeutically effective amount of ATR-101 to the patient.

In various aspects, a method for slowing or stopping progression of congenital adrenal hyperplasia in a patient is provided comprising administering a therapeutically effective amount of ATR-101 to the patient.

In various aspects, a method for slowing or stopping progression of hyperaldosteronism in a patient is provided comprising administering a therapeutically effective amount of ATR-101 to the patient.

In various aspects, a method for slowing or stopping progression of Conn syndrome in a patient is provided comprising administering a therapeutically effective amount of ATR-101 to the patient.

In various aspects, a method for slowing or stopping progression of unilateral aldosterone-producing adenoma in a patient is provided comprising administering a therapeutically effective amount of ATR-101 to the patient.

In various aspects, a method for slowing or stopping progression of bilateral adrenal hyperplasia (or idiopathic hyperaldosteronism (IHA)) in a patient is provided comprising administering a therapeutically effective amount of ATR-101 to the patient.

In various aspects, a method for slowing or stopping progression of renin-responsive adenoma in a patient is provided comprising administering a therapeutically effective amount of ATR-101 to the patient.

In various aspects, a method for slowing or stopping progression of primary adrenal hyperplasia in a patient is provided comprising administering a therapeutically effective amount of ATR-101 to the patient.

In various aspects, a method for slowing or stopping progression of glucocorticoid-remediable aldosteronism (GRA) in a patient is provided comprising administering a therapeutically effective amount of ATR-101 to the patient.

In various aspects, a method for slowing or stopping progression of 21-hydroxylase deficiency in a patient is provided comprising administering a therapeutically effective amount of ATR-101 to the patient.

Preventing

In various aspects, a method for preventing increased hormone production in a patient is provided comprising administering a therapeutically effective amount of ATR-101 to the patient.

In various aspects, a method for preventing benign adenoma in a patient is provided comprising administering a therapeutically effective amount of ATR-101 to the patient.

In various aspects, a method for preventing adrenocortical carcinoma in a patient is provided comprising administering a therapeutically effective amount of ATR-101 to the patient.

In various aspects, a method for preventing metastatic adrenocortical carcinoma in a patient is provided comprising administering a therapeutically effective amount of ATR-101 to the patient.

In various aspects, a method for preventing Cushing's syndrome in a patient is provided comprising administering a therapeutically effective amount of ATR-101 to the patient.

In various aspects, a method for preventing excess cortisol production in a patient is provided comprising administering a therapeutically effective amount of ATR-101 to the patient.

In various aspects, a method for preventing progression symptoms associated with excess cortisol production in a patient is provided comprising administering a therapeutically effective amount of ATR-101 to the patient.

In various aspects, a method for preventing congenital adrenal hyperplasia in a patient is provided comprising administering a therapeutically effective amount of ATR-101 to the patient.

In various aspects, a method for preventing hyperaldosteronism in a patient is provided comprising administering a therapeutically effective amount of ATR-101 to the patient.

In various aspects, a method for preventing Conn syndrome in a patient is provided comprising administering a therapeutically effective amount of ATR-101 to the patient.

In various aspects, a method for preventing unilateral aldosterone-producing adenoma in a patient is provided comprising administering a therapeutically effective amount of ATR-101 to the patient.

In various aspects, a method for preventing bilateral adrenal hyperplasia (or idiopathic hyperaldosteronism (IHA)) in a patient is provided comprising administering a therapeutically effective amount of ATR-101 to the patient.

In various aspects, a method for preventing renin-responsive adenoma in a patient is provided comprising administering a therapeutically effective amount of ATR-101 to the patient.

In various aspects, a method for preventing primary adrenal hyperplasia in a patient is provided comprising administering a therapeutically effective amount of ATR-101 to the patient.

In various aspects, a method for preventing glucocorticoid-remediable aldosteronism (GRA) in a patient is provided comprising administering a therapeutically effective amount of ATR-101 to the patient.

In various aspects, a method for preventing 21-hydroxylase deficiency in a patient is provided comprising administering a therapeutically effective amount of ATR-101 to the patient.

Reversing

In various aspects, a method for reversing hormone production in a patient is provided comprising administering a therapeutically effective amount of ATR-101 to the patient.

In various aspects, a method for reversing benign adenoma in a patient is provided comprising administering a therapeutically effective amount of ATR-101 to the patient.

In various aspects, a method for reversing adrenocortical carcinoma in a patient is provided comprising administering a therapeutically effective amount of ATR-101 to the patient.

In various aspects, a method for reversing metastatic adrenocortical carcinoma in a patient is provided comprising administering a therapeutically effective amount of ATR-101 to the patient.

In various aspects, a method for reversing Cushing's syndrome in a patient is provided comprising administering a therapeutically effective amount of ATR-101 to the patient.

In various aspects, a method for reversing excess cortisol production in a patient is provided comprising administering a therapeutically effective amount of ATR-101 to the patient.

In various aspects, a method for reversing congenital adrenal hyperplasia in a patient is provided comprising administering a therapeutically effective amount of ATR-101 to the patient.

In various aspects, a method for reversing hyperaldosteronism in a patient is provided comprising administering a therapeutically effective amount of ATR-101 to the patient.

In various aspects, a method for reversing Conn syndrome in a patient is provided comprising administering a therapeutically effective amount of ATR-101 to the patient.

In various aspects, a method for reversing unilateral aldosterone-producing adenoma in a patient is provided comprising administering a therapeutically effective amount of ATR-101 to the patient.

In various aspects, a method for reversing bilateral adrenal hyperplasia (or idiopathic hyperaldosteronism (IHA)) in a patient is provided comprising administering a therapeutically effective amount of ATR-101 to the patient.

In various aspects, a method for reversing renin-responsive adenoma in a patient is provided comprising administering a therapeutically effective amount of ATR-101 to the patient.

In various aspects, a method for reversing primary adrenal hyperplasia in a patient is provided comprising administering a therapeutically effective amount of ATR-101 to the patient.

In various aspects, a method for reversing glucocorticoid-remediable aldosteronism (GRA) in a patient is provided comprising administering a therapeutically effective amount of ATR-101 to the patient.

In various aspects, a method for reversing 21-hydroxylase deficiency in a patient is provided comprising administering a therapeutically effective amount of ATR-101 to the patient.

Compounds

Compounds useful in methods of the disclosure include, in various aspects, those that induce a state of quiescence in adrenal cortex cells. In various aspects, compounds and methods do not kill adrenal stem cells. In various aspects, compounds and methods of the disclosure selectively ablate the adrenal cortex cells. In various aspects, compounds of the disclosure selectively inhibit the enzymatic activity of cytochrome C oxidase (Complex IV) in adrenal cortex cells, and/or selectively inhibit respiration in target adrenal cortex cells. In various aspects, compounds and methods of the disclosure modulate hormone production in (and from) adrenal cortex cells.

In one embodiment, methods of the disclosure utilize an inhibitor of acyl-coenzyme A:cholesterol O-acyltransferase (ACAT; EC 2.3.1.26) designated as PD132301 or PD132301-2 (N-(2,6-bis(1-methylethyl)phenyl)-N'-((1-(4-(dimethylamino)phenyl)cyclopentyl)-methyl)urea hydrochloride; PD-132301-2; PD 132301-2; Urea, N-(2,6-bis(1-methylethyl)-phenyl)-N'-((1-(4-(dimethylamino)phenyl)-cyclopentyl)methyl)-, monohydrochloride). Prodrugs of PD132301, as wells as salts thereof, are also contemplated. The monohydrochloride salt of the free base, as depicted by the following structure, is referred to herein as "ATR-101".

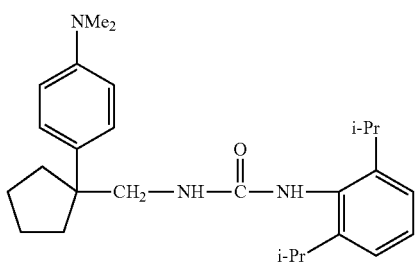 [SMILES: CC(C)c1cccc(C(C)C)c1NC(=O)NCC1(c2ccc(N(C)C)cc2)CCCC1]

ATR-101 may be made by techniques known in the art, including (for example) by the procedures disclosed by Trivedi, B. K., et al., *J. Med. Chem.*, 37(11):1652-1659, 1994 and/or U.S. Pat. No. 5,015,644. In addition to the monohydrochloride salt, other contemplated salt forms include salts which retain biological effectiveness and which are not biologically or otherwise undesirable, and which are formed with inorganic acids such as, but not limited to, hydrochloric acid, hydrobromic acid, sulfuric acid, nitric acid, phosphoric acid and the like, or with organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

Testing

It is understood in the art that a patient population to be targeted with a method or compound of the invention is identified through routine testing. In one embodiment, a target patient is identified as one wherein adrenocorticotropic hormone (ACTH levels) are low or suppressed, dehydroepiandrosterone (DHEA) levels are low or suppressed, aldosterone levels are high, cortisol levels are high, and/or potassium levels low.

With respect to high levels of cortisol, it is known in the art that cortisol can suppress DHEA and progesterone. It can also suppress thyroid activity. Cortisol can mobilize calcium from bones, and circulate it back into our blood stream. In various aspects, an excess of cortisol can cause bone loss and therefore osteoporosis. Excess cortisol can suppress the immune system and cause disease, including parasitic and viral diseases. For example, *Candida* and parasitic conditions can be caused by high cortisol since excess cortisol destroys friendly bacteria just like antibiotics do. High cortisol also elevates blood sugar which can initiate, or worsen, diabetic conditions. Thus, weight gain around the abdominal region is common from stress induced high cortisol.

Elevated cortisol can manifest with easy bruising, poor muscle tone or muscle wasting, poor wound healing, thin skin, stretch marks, excess scar tissue, development of fat pads, chronic yeast infections, accelerated skin aging, puffy flabby skin, water retention, moon face, memory loss and loss of general cognitive (learning) ability, and/or mood swings. Symptoms that suggest increased cortisol or other adrenal gland hormone production include fatty, rounded hump high on the back just below the neck (buffalo hump), obesity, stunted growth in height (short stature), virilization, including the appearance of male characteristics, including increased body hair (especially on the face), pubic hair, acne, and deepening of voice.

Co-Therapy

Methods provided contemplate co-therapy by administration of a second therapeutic agent, including known chemotherapeutics, targeting agents, adrenalysis agents, metformin, everolimus, and/or IGF1R antagonist. Methods involving co-therapy also include use of radiation therapy.

Clinical Trial Regimens

Methods contemplated include use of a compound in combination with other treatment methods currently involved, previously involved or expected to be involved in the future, in clinical trials.

For example, methods are provided involving administration of a compound with mitotane by mouth four times a day for 3 weeks. The regimen includes a 6-hour infusion of cisplatin on 2 days and 1-hour infusions of etoposide on 3 days and doxorubicin on 2 days in week 1. G-CSF is administered once a day beginning in week 1 and continuing until blood counts return to normal or an injection of pegfilgrastim once in week 1.

Methods are provided which include use of a compound with mitotane in patients who have undergone or will undergo radical resection.

Methods are contemplated including a compound of the disclosure with oral sorafenib 400 mg p.o. bid plus intravenous paclitaxel 60 mg/mq/weekly i.v.

Methods are provided which include a administering a compound with an antineoplaston. In some aspects, methods for the treatment of stage IV adrenal gland cancer are contemplated.

Methods are also contemplated for administering a compound with axitinib in individuals with aggressive or otherwise untreatable adrenocortical cancer.

Methods are contemplated utilizing a compound of the disclosure with sunitinib or temsirolimus. A method involving administration of a compound with sunitinib hydroxychloroquine administration is also contemplated.

Methods are also contemplated utilizing a compound of the disclosure and dovitinib (TKI-258), dosed on a flat scale of 500 mg/day on a 5 days on/2 days off schedule.

Methods are also contemplated utilizing a compound of the disclosure with antibody 8H9 injected into the lining of the abdomen or peritoneum, where the tumor is. Methods wherein radioactive iodine can be bound to this antibody to deliver radiation to the tumor are also contemplated.

Chemotherapeutic/Radiotherapeutic Agents

Examples of suitable chemotherapeutic and radiotherapeutic agents include, but are not limited to: an antimetabolite; a DNA-damaging agent; a cytokine useful as a chemotherapeutic agent; a covalent DNA-binding drug; a topoisomerase inhibitor; an antimitotic agent; an anti-tumor antibiotic; a differentiation agent; an alkylating agent; a methylating agent; a hormone or hormone antagonist; a nitrogen mustard; a radiosensitizer; a photosensitizer; a radiation source, optionally together with a radiosensitizer or photosensitizer; or other commonly used therapeutic agents.

Chemotherapeutic agents contemplated for use include, without limitation, alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabino side (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actinomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin, Pt(IV) and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocortico steroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

In some embodiments, a chemotherapeutic agent is co-administered or co-formulated wherein the chemotherapeutic agent is selected from the group consisting of 5-fluorouracil (5-FU), Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon β-2a; interferon β-2b; interferon β-n1; interferon β-n3; interferon β-I a; interferon β-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other chemotherapeutic agents include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; anagrelide; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; pothromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; zanoterone; zilascorb; and zinostatin stimalamer.

Cytokines

Cytokines that are effective in inhibiting carcinoma growth and metastasis are also contemplated for use in the combination therapy. Such cytokines, lymphokines, or other hematopoietic factors include, but are not limited to, M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN-α or IFN-γ, TNFα, TNF1, TNF2, G-CSF, Meg-CSF, GM-CSF, SCF, MIP-1 LIF, c-kit ligand, thrombopoietin, stem cell factor, and erythropoietin.

Co-Stimulatory Compounds

Methods involving co-therapy with other stimulatory molecules are also contemplated. Stimulatory molecules include CD40, B7-1, B7-2, CD54, members of the ICAM family (including ICAM-1, -2, or -3), CD58, SLAM ligands, polypeptides that bind heat stable antigen, polypeptides which bind to members of the TNF receptor family (including without limitation 4-1BBL, TRAF-1, TRAF-2, TRAF-3, OX40L, TRAF-5, CD70), CD 154, chemokines including without limitation CCL3, CCL5 CXCL10 and CCL7.

Administration

Standard of Care

In some embodiments, the methods described herein further comprise administering a standard of care cancer therapy to the subject. In the context of methods of the invention, "standard of care" refers to a treatment that is generally accepted by clinicians for a certain type of patient diagnosed with a type of illness.

Routes of Administration

The compound is administered by any suitable means, either systemically or locally, including via parenteral, subcutaneous, intrapulmonary, intramuscular, oral, and intranasal. Parenteral routes include intravenous, intraarterial, epidural, and intrathecal administration. In various aspects, the compound is administered by pulse infusion. Other administration methods are contemplated, including topical, particularly transdermal, transmucosal, rectal, oral or local administration.

Pharmaceutical Compositions/Formulation

Another aspect of the disclosure provides a pharmaceutical composition for treating a condition. In still another aspect of the disclosure, a composition comprising ATR-101 and a second therapeutic agent in a unit dose is provided.

One or more other pharmaceutically acceptable components as described in Remington's Pharmaceutical Sciences 16th edition, Osol, A. Ed. (1980) is included in the formulation provided that they do not adversely affect the desired characteristics of the formulation. Examples of formulations for a pharmaceutical composition include, without limitation, solutions, suspensions, powders, granules, tablets, capsules, pills, lozenges, chews, creams, ointments, gels, liposome preparations, nanoparticulate preparations, injectable preparations, enemas, suppositories, inhalable powders, sprayable liquids, aerosols, patches, depots and implants. In various aspects, a pharmaceutical composition formulation is in the form of a tablet or a capsule. Tablets are, in various aspects, uncoated or comprise a core that is coated, for example with a nonfunctional film or a release-modifying or enteric coating. In various aspects, capsules have hard or soft shells comprising, for example, gelatin and/or HPMC, optionally together with one or more plasticizers. Lyophilized formulations or aqueous solutions are contemplated. Sustained release formulations are also provided.

Various components of a pharmaceutical composition provided depend on the chosen route of administration and desired delivery method.

Carriers

Suitable carriers include any material which, when combined with the compound, retains the activity and is nonreactive with the subject's immune system. Examples include, but are not limited to, any of a number of standard pharmaceutical carriers. A variety of aqueous carriers are contemplated and include, without limitation, water, buffered water, physiological saline, 0.4% saline, and 0.3% glycine.

Stabilizers

In various aspects, a pharmaceutical composition formulation includes a protein for enhanced stability, such as and without limitation, albumin, lipoprotein, and globulin.

Diluents

In various aspects, a pharmaceutical composition formulation includes a diluent, either individually or in combination, such as, and without limitation, lactose, including anhydrous lactose and lactose monohydrate; lactitol; maltitol; mannitol; sorbitol; xylitol; dextrose and dextrose monohydrate; fructose; sucrose and sucrose-based diluents such as compressible sugar, confectioner's sugar and sugar spheres; maltose; inositol; hydrolyzed cereal solids; starches (e.g., corn starch, wheat starch, rice starch, potato starch, tapioca starch, etc.), starch components such as amylose and dextrates, and modified or processed starches such as pregelatinized starch; dextrins; celluloses including powdered cellulose, microcrystalline cellulose, silicified microcrystalline cellulose, food grade sources of α- and amorphous cellulose and powdered cellulose, and cellulose acetate; calcium salts including calcium carbonate, tribasic calcium phosphate, dibasic calcium phosphate dihydrate, monobasic calcium sulfate monohydrate, calcium sulfate and granular calcium lactate trihydrate; magnesium carbonate; magnesium oxide; bentonite; kaolin; sodium chloride; and the like.

Diluents, if present, typically constitute in total about 5% to about 99%, about 10% to about 85%, or about 20% to about 80%, by weight of the composition. The diluent or diluents selected exhibit suitable flow properties and, where tablets are desired, compressibility.

Binding Agents

In various aspects, a pharmaceutical composition formulation includes binding agents or adhesives which are useful excipients, particularly where the composition is in the form of a tablet. Such binding agents and adhesives should impart sufficient cohesion to the blend being formulated in a tablet to allow for normal processing operations such as sizing, lubrication, compression and packaging, but still allow the tablet to disintegrate and the compound to be absorbed upon ingestion. Suitable binding agents and adhesives include, either individually or in combination, acacia; tragacanth; glucose; polydextrose; starch including pregelatinized starch; gelatin; modified celluloses including methylcellulose, carmellose sodium, hydroxypropylmethylcellulose (HPMC or hypromellose), hydroxypropylcellulose, hydroxyethylcellulose and ethylcellulose; dextrins including maltodextrin; zein; alginic acid and salts of alginic acid, for example sodium alginate; magnesium aluminum silicate; bentonite; polyethylene glycol (PEG); polyethylene oxide; guar gum; polysaccharide acids; polyvinylpyrrolidone (povidone), for example povidone K-15, K-30 and K-29/32; polyacrylic acids (carbomers); polymethacrylates; and the like. One or more binding agents and/or adhesives, if present, constitute in various aspects, in total about 0.5% to about 25%, for example about 0.75% to about 15%, or about 1% to about 10%, by weight of the composition.

Buffers

In various aspects, an aqueous pharmaceutical composition formulation of the compound includes a buffer. Examples of buffers include acetate (e.g., sodium acetate), succinate (such as sodium succinate), gluconate, histidine, citrate and other organic acid buffers. The buffer concentration can be from about 1 mM to about 200 mM, or from about 10 mM to about 60 mM, depending, for example, on the buffer and the desired isotonicity of the formulation. In various aspects, an aqueous pharmaceutical composition formulation of the compound is prepared in a pH-buffered solution, for example, at pH ranging from about 4.5 to about 8.0, or from about 4.8 to about 6.5, or from about 4.8 to about 5.5, or alternatively about 5.0.

Disintegrants

In various aspects, a pharmaceutical composition formulation includes a disintegrant.

Suitable disintegrants include, either individually or in combination, starches including pregelatinized starch and sodium starch glycolate; clays; magnesium aluminum silicate; cellulose-based disintegrants such as powdered cellulose, microcrystalline cellulose, methylcellulose, low-substituted hydroxypropylcellulose, carmellose, carmellose calcium, carmellose sodium and croscarmellose sodium; alginates; povidone; crospovidone; polacrilin potassium; gums such as agar, guar, locust bean, karaya, pectin and tragacanth gums; colloidal silicon dioxide; and the like. One or more disintegrants, if present, typically constitute in total about 0.2% to about 30%, for example about 0.2% to about 10%, or about 0.2% to about 5%, by weight of the composition.

Wetting Agents

In various aspects, a pharmaceutical composition formulation includes a wetting agent. Wetting agents, if present, are normally selected to maintain the compound in close association with water, a condition that is believed to improve bioavailability of the composition. Non-limiting examples of surfactants that can be used as wetting agents include, either individually or in combination, quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10 and octoxynol 9; poloxamers (polyoxyethylene and polyoxypropylene block copolymers); polyoxyethylene fatty acid glycerides and oils, for example polyoxyethylene (8) caprylic/capric mono- and diglycerides, polyoxyethylene (35) castor oil and polyoxyethylene (40) hydrogenated castor oil; polyoxyethylene alkyl ethers, for example ceteth-10, laureth-4, laureth-23, oleth-2, oleth-10, oleth-20, steareth-2, steareth-10, steareth-20, steareth-100 and polyoxyethylene (20) cetostearyl ether; polyoxyethylene fatty acid esters, for example polyoxyethylene (20) stearate, polyoxyethylene (40) stearate and polyoxyethylene (100) stearate; sorbitan esters; polyoxyethylene sorbitan esters, for example polysorbate 20 and polysorbate 80; propylene glycol fatty acid esters, for example propylene glycol laurate; sodium lauryl sulfate; fatty acids and salts thereof, for example oleic acid, sodium oleate and triethanolamine oleate; glyceryl fatty acid esters, for example glyceryl monooleate, glyceryl monostearate and glyceryl palmitostearate; sorbitan esters, for example sorbitan monolaurate, sorbitan monooleate, sorbitan monopalmitate and sorbitan monostearate; tyloxapol; and the like. One or more wetting agents, if present, typically constitute in total about 0.25% to about 15%, preferably about 0.4% to about 10%, and more preferably about 0.5% to about 5%, by weight of the composition.

Lubricants

In various aspects, a pharmaceutical composition formulation includes a lubricant. Lubricants reduce friction between a tableting mixture and tableting equipment during compression of tablet formulations. Suitable lubricants include, either individually or in combination, glyceryl behenate; stearic acid and salts thereof, including magnesium, calcium and sodium stearates; hydrogenated vegetable oils; glyceryl palmitostearate; talc; waxes; sodium benzoate; sodium acetate; sodium fumarate; sodium stearyl fumarate; PEGs (e.g., PEG 4000 and PEG 6000); poloxamers; polyvinyl alcohol; sodium oleate; sodium lauryl sulfate; magnesium lauryl sulfate; and the like. One or more lubricants, if present, typically constitute in total about 0.05% to about 10%, for example about 0.1% to about 8%, or about 0.2% to about 5%, by weight of the composition. Magnesium stearate is a particularly useful lubricant.

Anti-Adherents

In various aspects, a pharmaceutical composition formulation includes an anti-adherent. Anti-adherents reduce sticking of a tablet formulation to equipment surfaces. Suitable anti-adherents include, either individually or in combination, talc, colloidal silicon dioxide, starch, DL-leucine, sodium lauryl sulfate and metallic stearates. One or more anti-adherents, if present, typically constitute in total about 0.1% to about 10%, for example about 0.1% to about 5%, or about 0.1% to about 2%, by weight of the composition.

Glidants

In various aspects, a pharmaceutical composition formulation includes a glidant. Glidants improve flow properties and reduce static in a tableting mixture. Suitable glidants include, either individually or in combination, colloidal silicon dioxide, starch, powdered cellulose, sodium lauryl sulfate, magnesium trisilicate and metallic stearates. One or more glidants, if present, typically constitute in total about 0.1% to about 10%, for example about 0.1% to about 5%, or about 0.1% to about 2%, by weight of the composition.

Tonicity Agents

In various aspects, a pharmaceutical composition formulation includes a tonicity agent. A tonicity agent may be included in the formulation for stabilization. Exemplary tonicity agents include polyols, such as mannitol, sucrose or trehalose. Preferably, the aqueous formulation is isotonic, although hypertonic or hypotonic solutions are contemplated. Exemplary concentrations of the polyol in the formulation may range from about 1% to about 15% w/v.

Surfactants

In various aspects, a pharmaceutical composition formulation includes a surfactant. A surfactant may also be added to reduce aggregation of the compound and/or to minimize the formation of particulates in the formulation and/or to reduce adsorption. Exemplary surfactants include nonionic surfactants such as polysorbates (e.g., polysorbate 20 or polysorbate 80) or poloxamers (e.g., poloxamer 188). Exemplary concentrations of surfactant may range from about 0.001% to about 0.5%, or from about 0.005% to about 0.2%, or alternatively from about 0.004% to about 0.01% w/v.

Preservatives

In various aspects, a pharmaceutical composition formulation is essentially free of one or more preservatives, such as benzyl alcohol, phenol, m-cresol, chlorobutanol and benzethonium. In other aspects, a preservative is included in the formulation, e.g., at concentrations ranging from about 0.1% to about 2%, or alternatively from about 0.5% to about 1%.

Sustained-Release Formulations

Sustained-release pharmaceutical composition formulations are also provided. Suitable examples of sustained-release preparations include semipermeable matrices of solid hydrophobic polymers containing the antibody, which matrices are in the form of shaped articles, including without limitation films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The active ingredients may also be entrapped in a microcapsule prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nano capsules) or in macroemulsions. Such techniques are disclosed in Remington's Pharmaceutical Sciences 16th edition, Osol, A. Ed. (1980).

Lyophilized Formulations

Also provided are pharmaceutical compositions in a lyophilized formulation. The resulting "lyophilized cake" is reconstituted prior to use. Reconstitution of the lyophilized cake adds a volume of aqueous solution, typically equivalent to the volume removed during lyophilization.

Dosages

The amount of the compound to be administered, and other administration parameters such as frequency and duration of therapy, depend on the compound or prodrug intended for use, and on other factors such as the route of administration, dose intervals, excretion rate, formulation of the compound, the recipient, age, body weight, sex, diet, medical history, and general state (e.g., health) of the subject being treated of the recipient, the severity of the disease, and/or the size, malignancy and invasiveness of a tumor to be treated The compound is thus administered at a dosage sufficient to achieve a desired therapeutic or prophylactic effect and is determined on a case-by-case basis.

In some embodiments, the compound is administered at a dosage of about 1.0 µg/kg to about 100 mg/kg, about 0.01 mg/kg to about 100 mg/kg, about 0.01 mg/kg to about 50 mg/kg, about 0.01 mg/kg to about 30 mg/kg, about 0.01 mg/kg to about 10 mg/kg, about 0.01 mg/kg to about 5 mg/kg, about 0.05 mg/kg to about 10 mg/kg, about 0.1 mg/kg to about 200 mg/kg, about 0.1 mg/kg to about 50 mg/kg, about 0.1 mg/kg to about 10 mg/kg, about 0.5 mg/kg to about 25 mg/kg, about 1 mg/kg to about 10 mg/kg, or about 2 mg/kg to about 10 mg/kg.

Administration is contemplated in a regiment that is daily; two, three, or four times daily; alternating days; every third day; or 2, 3, 4, 5, or 6 times per week; weekly; twice a month; monthly or more or less frequently, as necessary, depending on the response or condition and the recipient tolerance of the therapy. Maintenance dosages over a longer period of time, such as 4, 5, 6, 7, 8, 10 or 12 weeks or longer are contemplated, and dosages may be adjusted as necessary. The progress of the therapy is monitored by conventional techniques and assays, and is within the skill in the art.

The following examples are given merely to illustrate the present invention and not in any way to limit its scope.

EXAMPLES

Example 1

To investigate the potential therapeutic effect of ATR-101 in a mouse model of adrenocortical carcinoma (ACC), xenografts of the human ACC-derived cell line H295R in SCID mice (6-7 week males) were established. After the xenografts had grown to measurable size, the mice were randomized in two groups. The treatment group was administered 300 mg/kg/day ATR-101 by oral gavage. The control group was administered the vehicle without ATR-101. The tumor size was measured using calipers before and on the indicated days after starting administration of ATR-101.

Four of the mice in the treatment group and two of the mice in the control group died within 2 days of transferring the mice to the biohazardous agent containment facility and initiating administration. The cause(s) of these deaths are unknown, but unrelated to ATR-101 treatment. These mice were excluded from the analysis.

One of the mice in the treatment group and two of the mice in the control group died six days after beginning treatment. The tumors of the mice surviving in the treatment group decreased in size by 50% (n=3, relative standard deviation 32%) at 8 days after the start of ATR-101 administration (FIG. 1, solid lines). Meanwhile, the tumors of the mice in the control group increased in size by 400% (n=4, relative standard deviation 160%) in the same period (FIG. 1, dashed lines). The reproducibility of tumor measurements was corroborated by successive measurements 2 and 1 days before starting administration and again 6 and 8 days after starting administration. The body condition score (BCS) of mice in the treatment group (3.0) was also higher than that of mice in the control group (2.0).

The deaths of a large proportion of the mice coincident with the start of administration of vehicle and of ATR-101 caused us to change the formulation of ATR-101 from in 10% DMSO, 0.9% NaCl, 0.5% CMC pH3.9, 0.2% Tween-20 (Formulation I) to 0.5% CMC pH 1.9, 0.2% Tween-20 (Formulation II) after the first week of ATR-101 administration (FIG. 1). The tumors of the mice in the treatment group resumed growth within two days of the change in formulation, but the sizes of the tumors in this group were significantly smaller than those of the mice in the control group 15 days after beginning of ATR-101 administration ($p<0.05$).

ATR-101 administration to mice with ACC-derived cell line xenografts rapidly and reproducibly caused regression of the xenograft to less than half of its size prior to the start of ATR-101 administration in all mice with tumors smaller than 300 mm$^3$. In two mice with tumors of 300 mm$^3$ and 900 mm$^3$ ATR-101 administration did not halt the tumor growth and the mice quickly became moribund. Regression of H295R cell xenografts has not been reported in previous studies using other agents, including mitotane as well as drugs presently in clinical trials (Barlaskar, F. M., et al., *J. Clin. Endocrinol. Metab.*, 94(1):204-12, 2009; Luconi, M., et al., *Endocr. Relat. Cancer*, 17(1):169-77, 2010). These results supported advancing ATR-101 to clinical trials subject to determination of the dose-response relationship and extension of toxicology studies to establish the therapeutic window for ATR-101.

In both experiments, the therapeutic effect of ATR-101 was maximal 6-8 days after the start of ATR-101 administration. In both experiments the tumors resumed growth 7-9 days after the start of ATR-101 administration and exceeded pre-treatment size 8-15 days after the start of ATR-101 administration. Some of the tumors in the treated mice reached a size comparable to the tumors in the control mice 15 days after the start of ATR-101 administration. The reason(s) for the resumption of tumor growth and the relapse of the mice are unknown. Because of the reproducibility of the time-course of the relapse and the rapid expansion to pre-treatment size, it is unlikely that the relapse is due to genetic changes in the tumor cells.

The H295R cell line is the one ACC-derived cell line that is generally accepted to retain many of the characteristics of ACC tumor cells. A single primary xenograft of ACC tumor cells isolated from a patient has been reported in the literature (Yamazaki, H., et al., *APMIS*, 106(7-12):1056-1060, 1998). The primary xenograft exhibited growth within 8 days of implantation. The small number of cases where primary ACC tumors are available makes studies using primary tumor cells difficult.

Example 2

To determine if the effects of ATR-101 on ACC-derived cell line xenotransplants were reproducible, the experiment using xenotransplants of the same H295R cell line in SCID mice (10-11 week males) were repeated.

Figure 2:
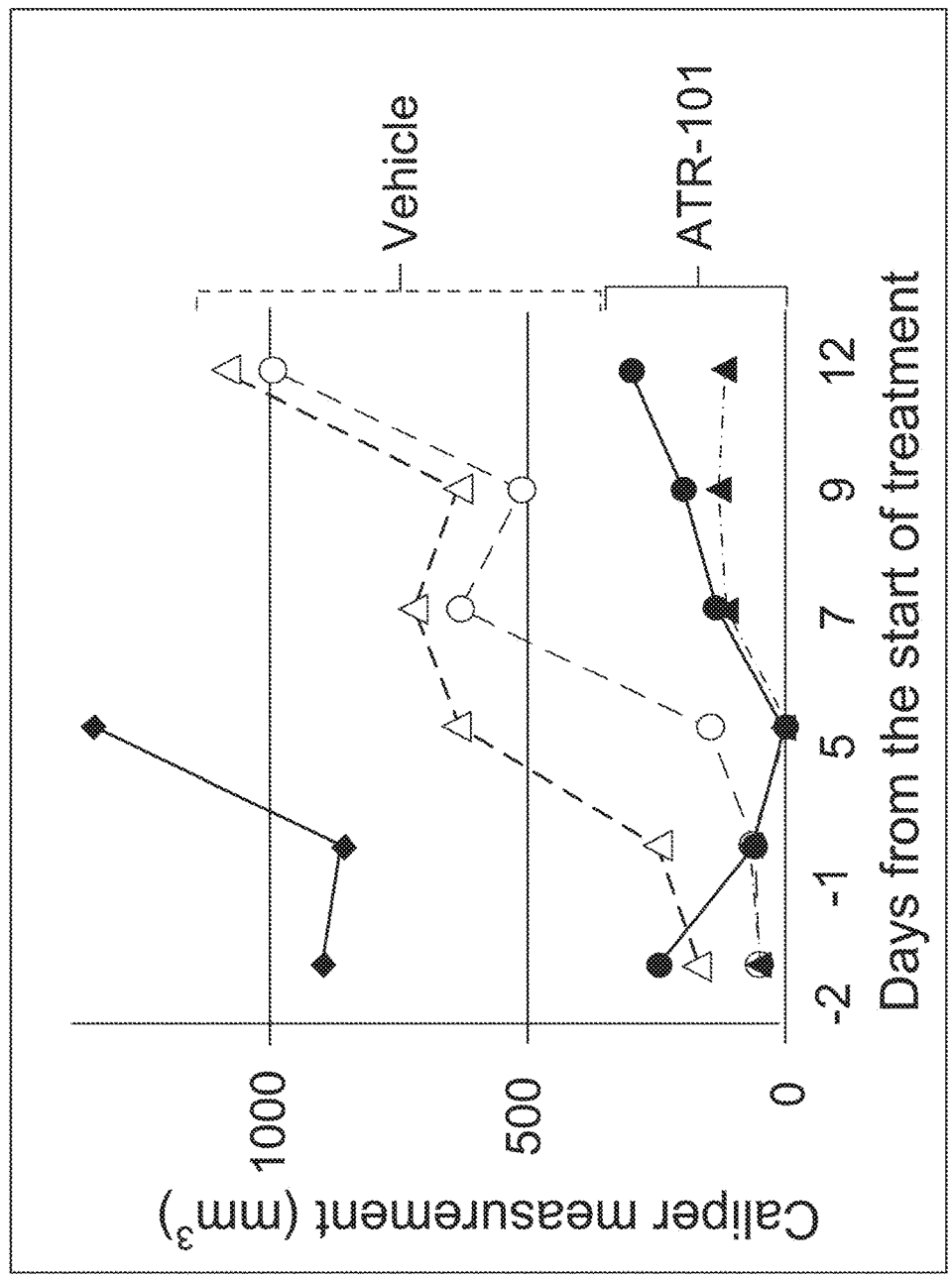
FIG. 2 depicts the effects of ATR-101 treatment on the sizes of H295R cell line xenotransplants in SCID mice. The solid lines with filled symbols represent mice administered 300 mg/kg/day ATR-101. The dashed lines and open symbols represent mice administered vehicle. ATR-101 was administered from two batches prepared separately in 10% DMSO, 0.9% NaCl, 0.5% CMC pH 3.9, 0.2% Tween-20 for days 1-6 and for the remainder of the experiment.

One of the mice in the treatment group had a large tumor produced by H295R cells implanted 4 weeks earlier. This mouse died 6 days after ATR-101 administration and is not included in the analysis. The tumors of the remaining mice in the treatment group (n=2) decreased to undetectable size at six days after the start of ATR-101 administration (FIG. 2). Meanwhile, the tumors of the mice in the control group (n=2) more than doubled in size. The tumors of the mice in the treatment group resumed growth within eight days after the start of ATR-101 administration. The tumors of the treated mice were one-eighth to one-third of the size of the tumors in the control mice 13 days after the start of ATR-101 administration. The resumption of tumor growth coincided with the switch to a new batch of ATR-101. This batch was prepared using ATR-101 from the same synthesis using the same protocol, with the exception that the preparation was not incubated overnight before the first dose was administered six days after the start of ATR-101 administration.

Both experiments were conducted with small numbers of mice in both the treatment and the control groups. There are several reasons for the small groups of mice used in these experiments. In addition to limited resources/personnel, only a portion of the mice (23/25) survived transport. Also, a subpopulation of the mice (16/23) developed tumors, and many mice died during the first two days after transfer into the containment facility for ATR-101 administration, leaving a small number with measurements after the start of treatment (10/16 and 5/7).

Figure 3:
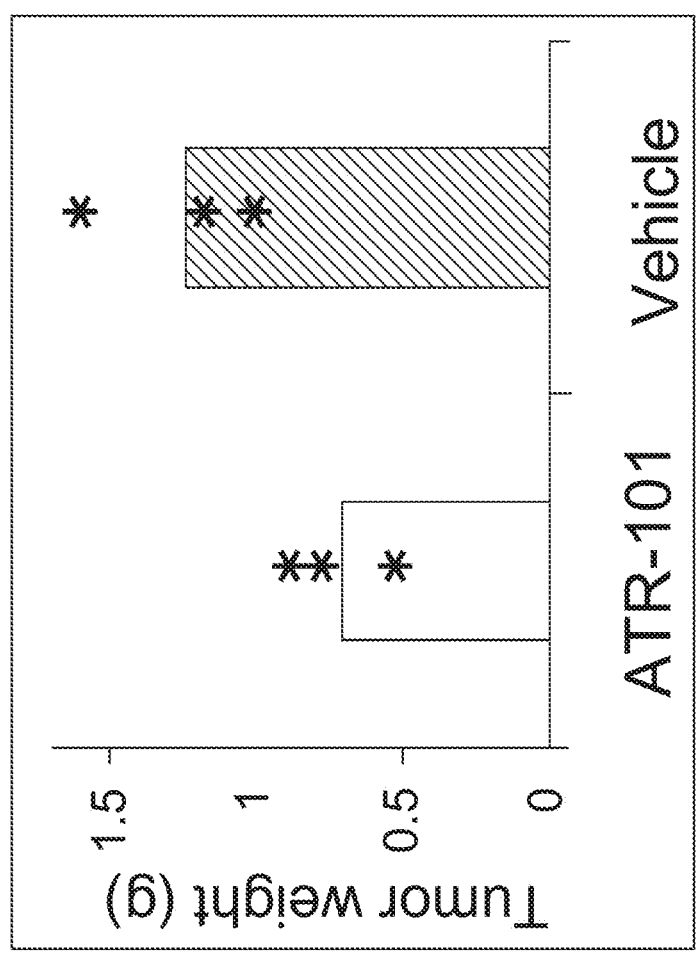
FIG. 3 depicts the results of the post-mortem analysis of the tumors and organs of mice from the treatment and control groups, and shows that the tumors of surviving mice in the treatment group were significantly smaller than the tumors of mice in the control group.

Post-mortem analysis of the tumors and organs of mice from the treatment and control groups of the first experiment confirmed that the tumors of surviving mice in the treatment group (mean 0.71 g, standard deviation of the mean 0.13 g) were significantly ($p<0.05$) smaller than the tumors of mice in the control group (mean 1.23 g, standard deviation of the mean 0.28 g) (FIG. 3). Tumor morphology was not detectably different between the treatment and control groups. The total body weight of the mice in the treatment group (mean 24 g, standard deviation of the mean 1 g) was significantly higher than that of mice in the control group (mean 19 g, standard deviation of the mean 3 g). This difference in body weight could reflect the greater tumor burden of mice in the control group.

Example 3

Figure 4:
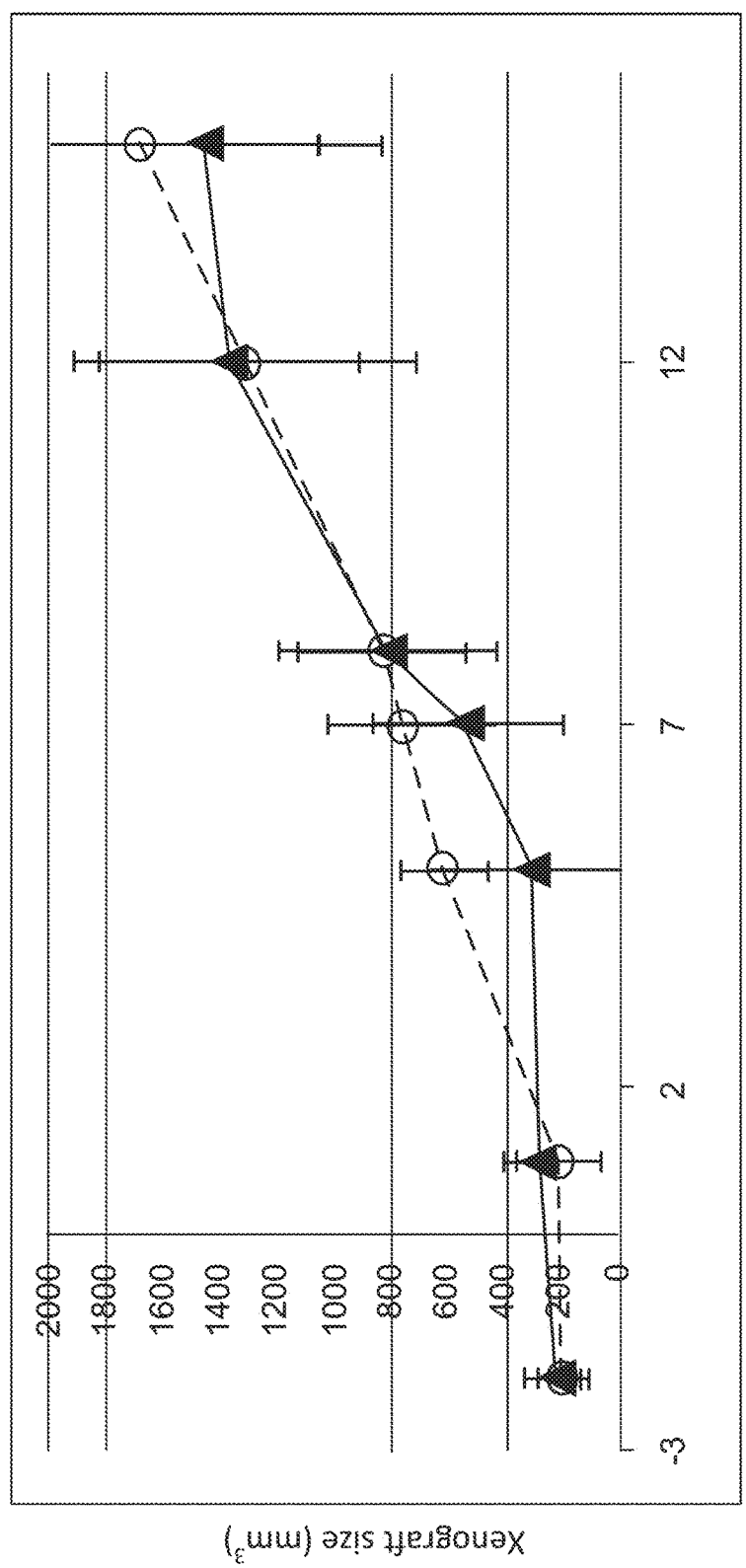
FIG. 4 depicts xenograft size as a function of time after start of oral administration of ATR-101 (triangles) versus control mice treated with vehicle (circles).

Xenograft size was measured using calipers as a function of time after the start of oral administration of 300 mg/kg/day ATR-101 (triangles) versus control mice treated with vehicle (circles) (FIG. 4). The data show the average and standard deviation of 9 and 10 mice in each group. One mouse included in the treatment group was eliminated because the abdominal location of the xenograft prevented accurate measurement of its size. The 20 mice were randomized between the treatment and control arms of the study. The xenografts were produced by subcutaneous injection of 100,000,000 H295R cells in each mouse.

Example 4

Figure 5:
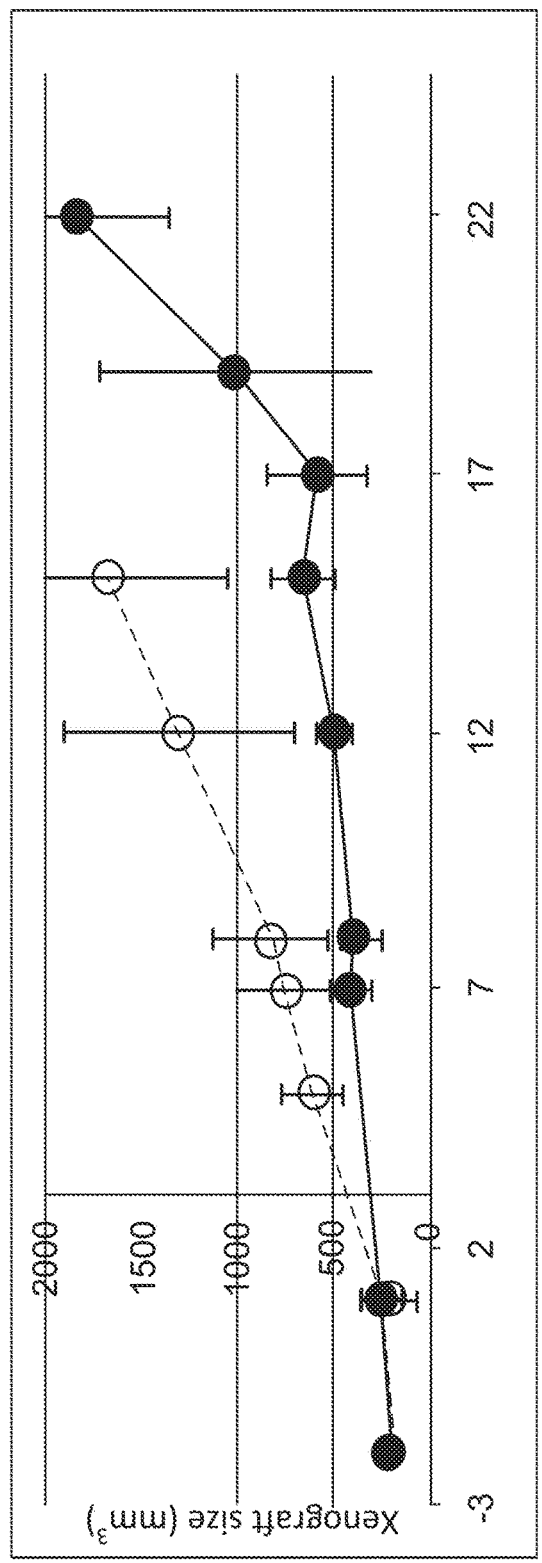
FIG. 5 depicts xenograft size as a function of time after start of oral administration of ATR-101 in combination with metformin (spheres) versus control mice treated with vehicle (circles).

Xenograft size was measured using calipers as a function of time after the start of oral administration of 300 mg/kg/day ATR-101+300 mg/kg/day metformin (spheres) versus control mice treated with vehicle (circles) (FIG. 5). The data show the average and standard deviation of 3 and 10 mice in each group. The two groups of mice were injected and reared together, but were not randomized as part of the same group of mice The xenografts were produced by subcutaneous injection of 100,000,000 H295R cells in each mouse.

Example 5

Figure 6:
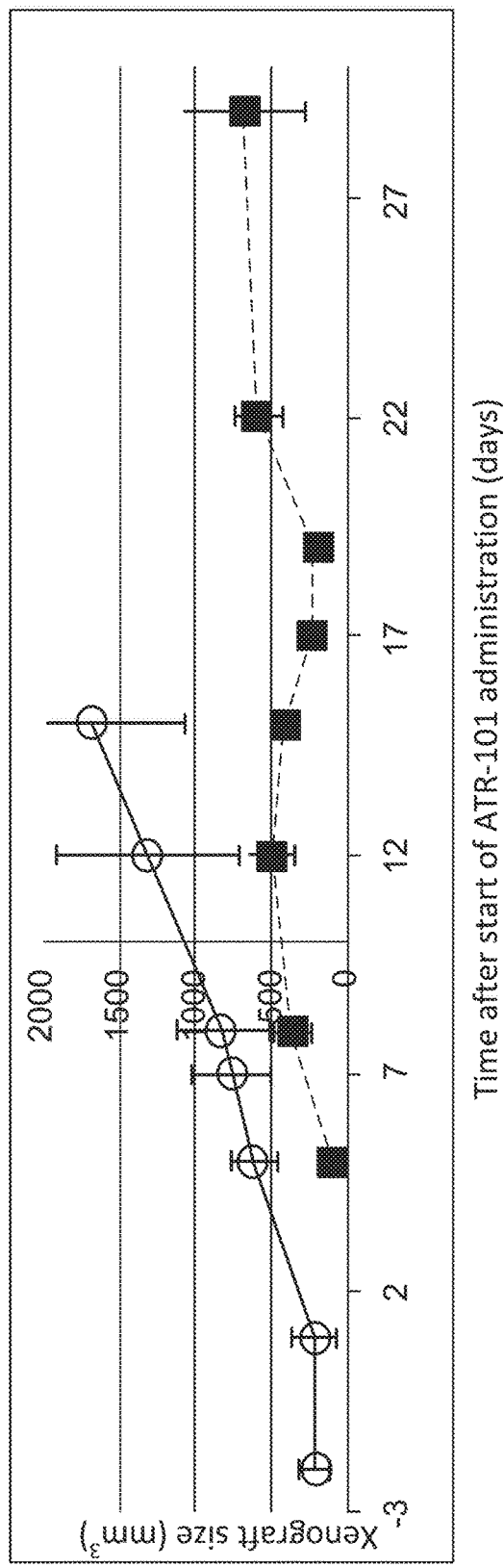
FIG. 6 depicts xenograft size as a function of time after start of oral administration of ATR-101 in combination with everolimus (squares) versus control mice treated with vehicle (circles).

Xenograft size was measured using calipers as a function of time after the start of oral administration of 300 mg/kg/day PD132301-02+4 mg/kg/day everolimus (squares) versus control mice treated with vehicle (circles) (FIG. 6). The data show the average and standard deviation of 3 and 10 mice in each group. The two groups of mice were injected and reared together, but were not randomized as part of the same group of mice The xenografts were produced by subcutaneous injection of 100,000,000 H295R cells in each mouse.

Example 6

To investigate the potential therapeutic benefit of ATR-101 in the establishment of ACC xenografts in a mouse model of ACC, ACC-derived cell line H295R was injected in SCID mice (6-7 week males). $1 \times 10^8$ cells in 0.2 ml DMEM were injected under the skin in the right dorsal flank regions of SCID mice. Two weeks after injection, the mice were randomized in groups of 10. ATR-101 was administered at 700 mg/kg/day for 4 days, followed by 300 mg/kg/day by oral gavage in 10% DMSO, 0.5% CMC, 0.9% NaCl, 0.2% Tween, pH 3. Control mice were administered vehicle. The tumor size was measured using calipers three times a week. Urinary cortisol was measured at various time points after start of ATR-101 or vehicle administration.

Figure 7:
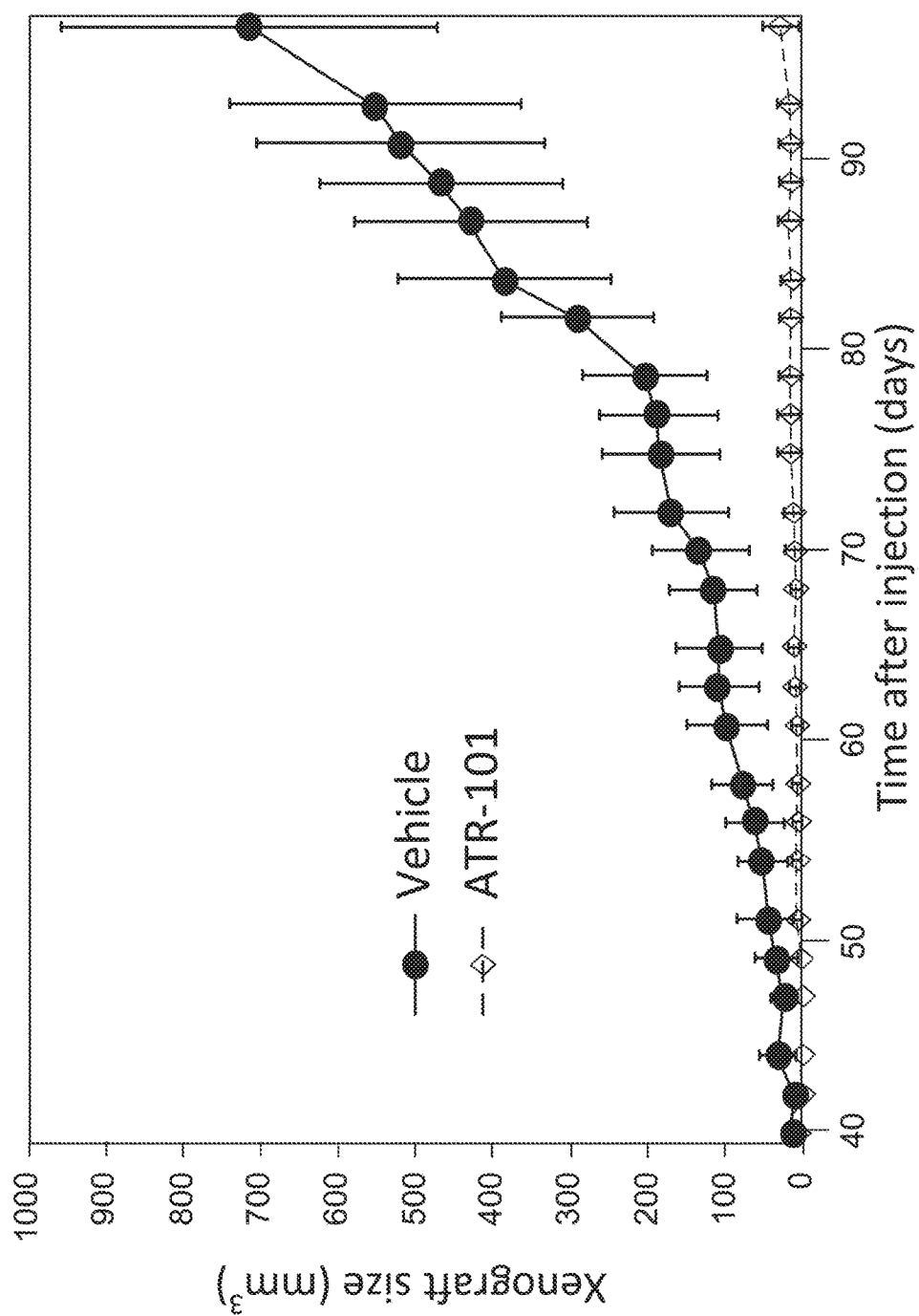
FIG. 7 depicts the effects of ATR-101 administration on ACC xenograft establishment. Randomized cohorts of 10 mice injected with H295R cells were administered 700 mg/kg/day ATR-101 for 4 days followed by 300 mg/kg/day ATR-101 or vehicle by gavage beginning 14 days after cell injection. The sizes of the xenografts were measured three times each week. The data show the mean and the standard deviation of the xenograft volume (ellipsoid model) at different times after injection.

Of the 10 mice treated with vehicle, 7 developed palpable xenografts within 50 days after injection. Five of the mice were euthanized as moribund with xenografts larger than 2,000 $mm^3$ by 100 days after injection. Of the 10 mice treated with ATR-101, 2 developed palpable xenografts and the median time until xenograft formation was more than twice as long as for the vehicle-treated group. All the mice were alive 100 days after injection, and the 2 xenografts had not grown to 500 $mm^3$ (FIG. 7). There was no significant difference in the body weights of the mice treated with vehicle versus ATR-101. ATR-101 treatment therefore inhibited xenograft establishment, reduced the rate of xenograft growth, and extended survival of SCID mice injected with ACC-derived cells.

Figure 8:
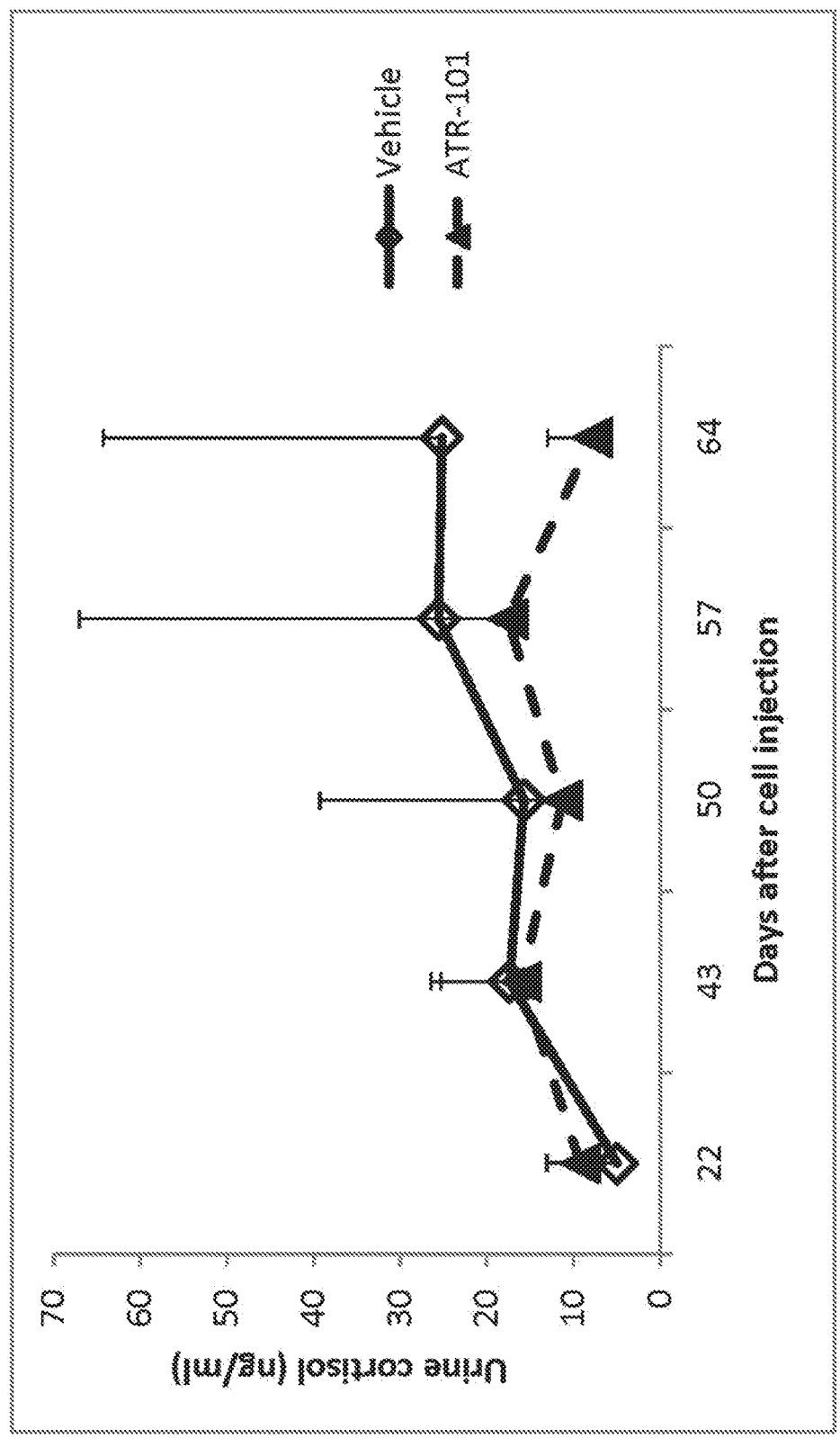
FIG. 8 depicts the urinary cortisol levels in mice with H295R xenotransplants treated with vehicle or ATR-101. Randomized cohorts of 10 mice injected with H295R cells were administered 700 mg/kg/day ATR-101 for 4 days followed by 300 mg/kg/day ATR-101 or vehicle by gavage beginning 14 days after cell injection. Urine was collected on the days indicated beginning at 22 days after cell injection (8 days after the start of ATR-101 or vehicle administration), and the cortisol levels were determined using a DetectX® cortisol assay kit (Arbor Assays).

Approximately 60% of all adrenocortical carcinomas exhibit signs of hormone excess, most commonly cortisol (Peppa et al., Cases J. 2:8951, 2009). In some cases, Cushing's syndrome may be caused by an ACC producing excessive cortisol. The original H295 cell line was isolated from an ACC which produced excessive cortisol (Gazdar et al., Cancer Res. 50:5488-5496, 1990). H295R cell line continues to exhibit cortisol production (Samandari et al., J. Endocrinol. 195:459-472, 2007). Urinary cortisol levels were measured several times starting 22 days after cell injection (8 days after the start of ATR-101 or vehicle administration) (FIG. 8). The urinary cortisol levels in mice treated with vehicle varied in relation to the sizes of their xenografts. The average urinary cortisol levels of mice treated with ATR-101 were lower than those of mice that were administered vehicle. Thus, ATR-101 treatment reduced the level of cortisol produced by H295R cells xenografted into SCID mice.

Example 7

Figure 9:
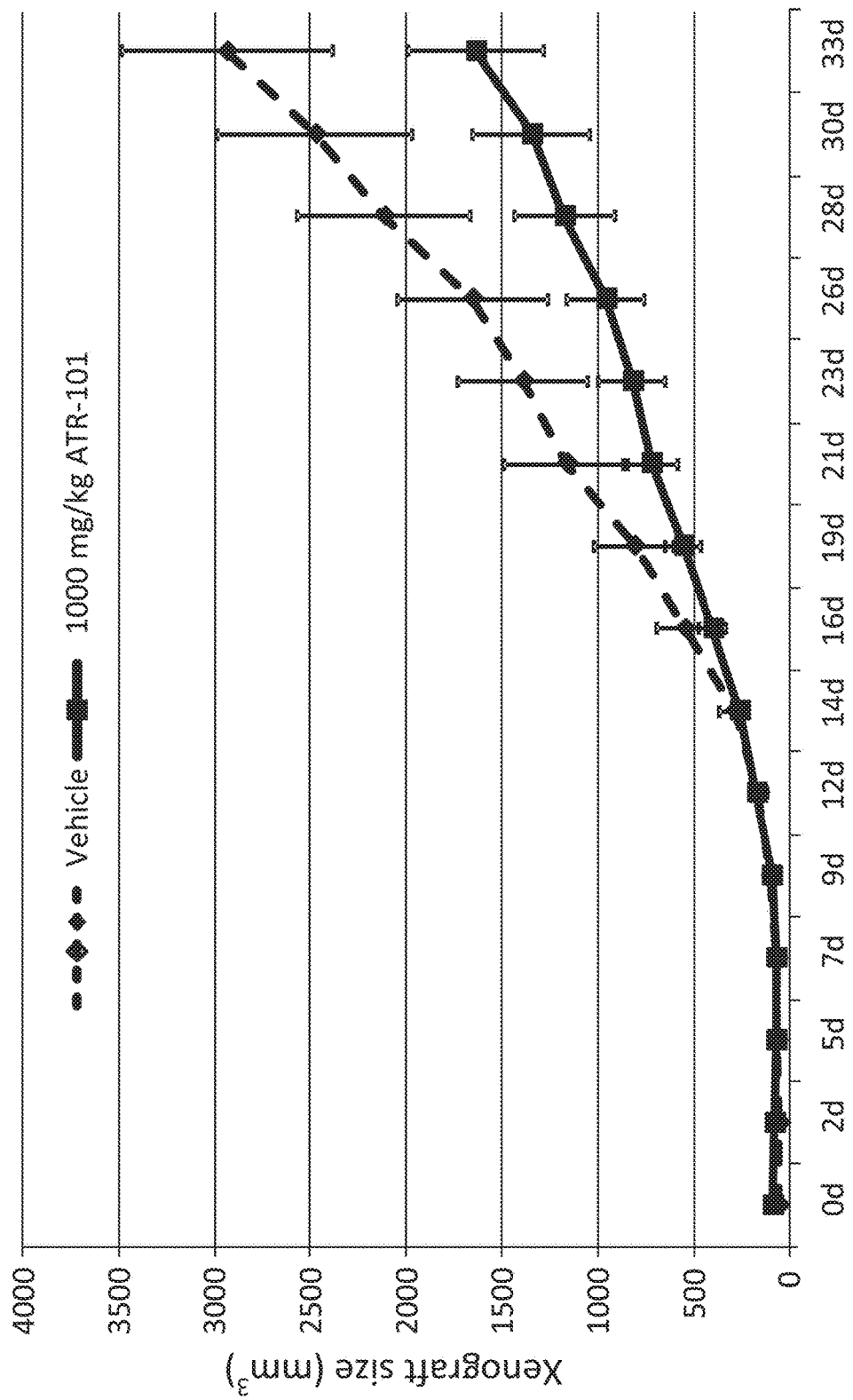
FIG. 9 depicts the effect of high dose of ATR-101 on sizes of H295R cell line xenotransplants in SCID mice. Xenograft size is shown as a function of time after start of oral administration of 1,000 mg/kg/day ATR-101 (squares) versus control mice treated with vehicle (diamonds).
Figure 10:
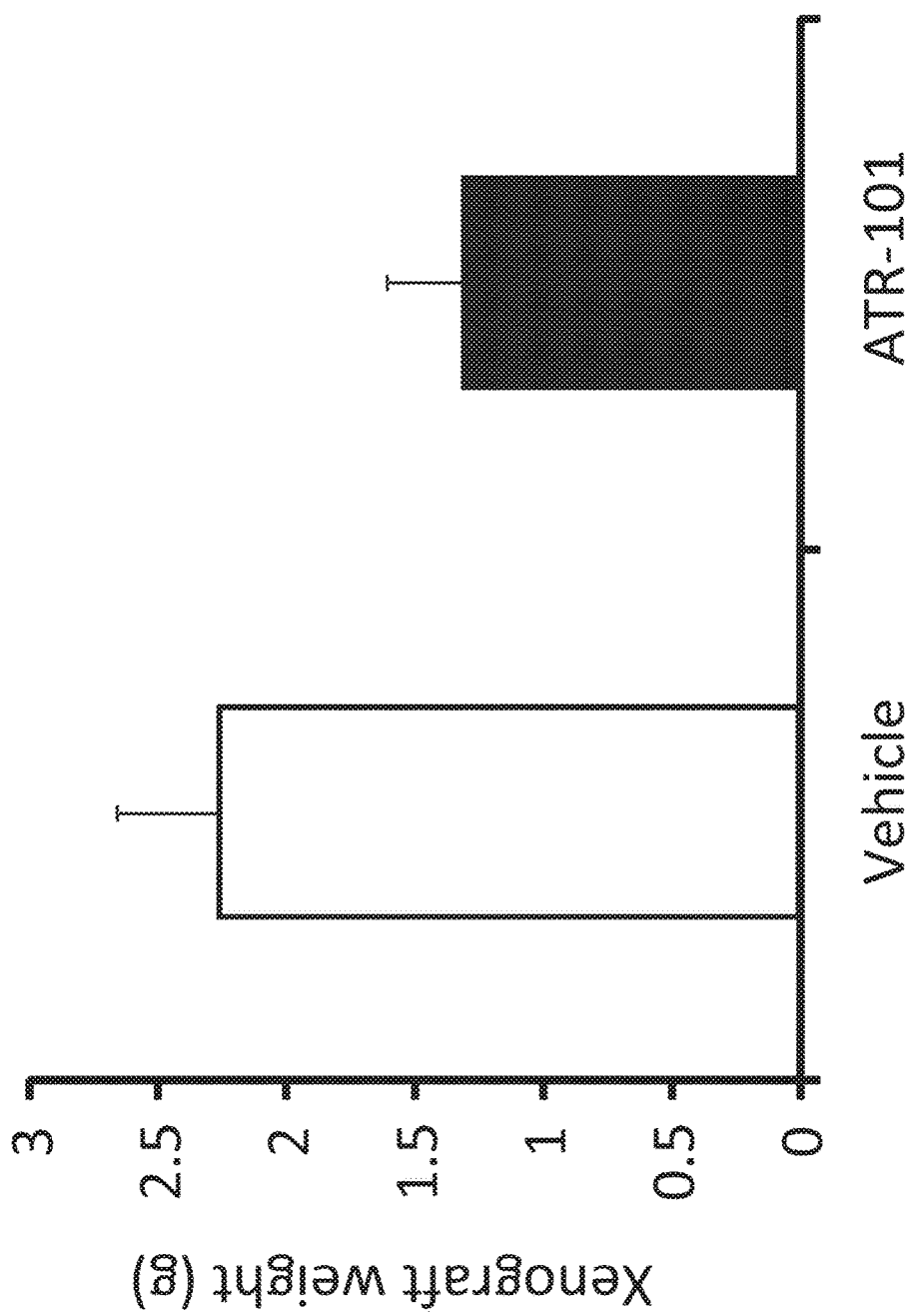
FIG. 10 depicts xenograft weights in mice treated with 1,000 mg/kg/day ATR-101 compared with vehicle treated mice.

The effects of a high dose of ATR-101 on ACC-derived xenotransplants in SCID mice were also studied. Xenografts were produced as previously described with 3 mice in the ATR-101 treated group and 3 mice in the control group. As shown in FIG. 9, xenograft size was measured using calipers as a function of time after the start of oral administration of 1,000 mg/kg/day ATR-101 (squares) versus control mice treated with vehicle (diamonds). ATR-101 administration at a high dose (1,000 mg/kg/day) significantly reduced tumor growth as compared to vehicle treated controls. As shown in FIG. 10, xenograft weights were measured in 1,000 mg/kg/day ATR-101 treated mice versus vehicle treated control mice.

Example 8

The mechanism of ATR-101 cytotoxicity was investigated by measuring its effects on the ATP levels and on the reducing activities of ACC-derived H295R cells grown in normal and cholesterol-depleted conditions.

To measure ATP levels and reducing potentials of H295R cells, these cells were cultured in 96-well flat bottom cell culture plates (BD Biosciences) plated at 50,000 cells in 100 µl. The cells were plated in DMEM media without glucose (GIBCO 11966)+10 mM galactose+5 mM sodium-HEPES+2 mM glutamine (addition)+1 mM sodium pyruvate+100 U/ml penicillin/streptomycin+either 0% or 5% fetal calf serum. After overnight (16-20 h) incubation, 20 µl of medium containing 5% fetal calf serum as well as the aliquots of ATR-101 required to produce the final concentrations were added to the cells. To measure ATP levels, 100 µl of the CellTiter-Glo® (Promega Corp., Madison, Wis.) reagent was added to lyse the cells at the indicated times, and luciferin luminescence was measured to determine the amount of ATP in the lysate. To measure reducing activity, PrestoBlue® Cell Viability reagent (Life Technologies Corp.) was added to the cells immediately after ATR-101. The cells were incubated at 37° C. with $CO_2$, and resorufin fluorescence was measured at the times indicated.

Addition of ATR-101 to H295R cells reduced the luminescence signal of the ATP-dependent luciferase assay in a time- and concentration-dependent manner (FIG. 11A). 16 µM ATR-101 had a half-maximal effect in 4 hours. In the same time, 64 µM ATR-101 reduced the luminescence signal by about 90%. These results indicate that ATR-101 caused rapid depletion of ATP in H295R cells.

Figure 11:
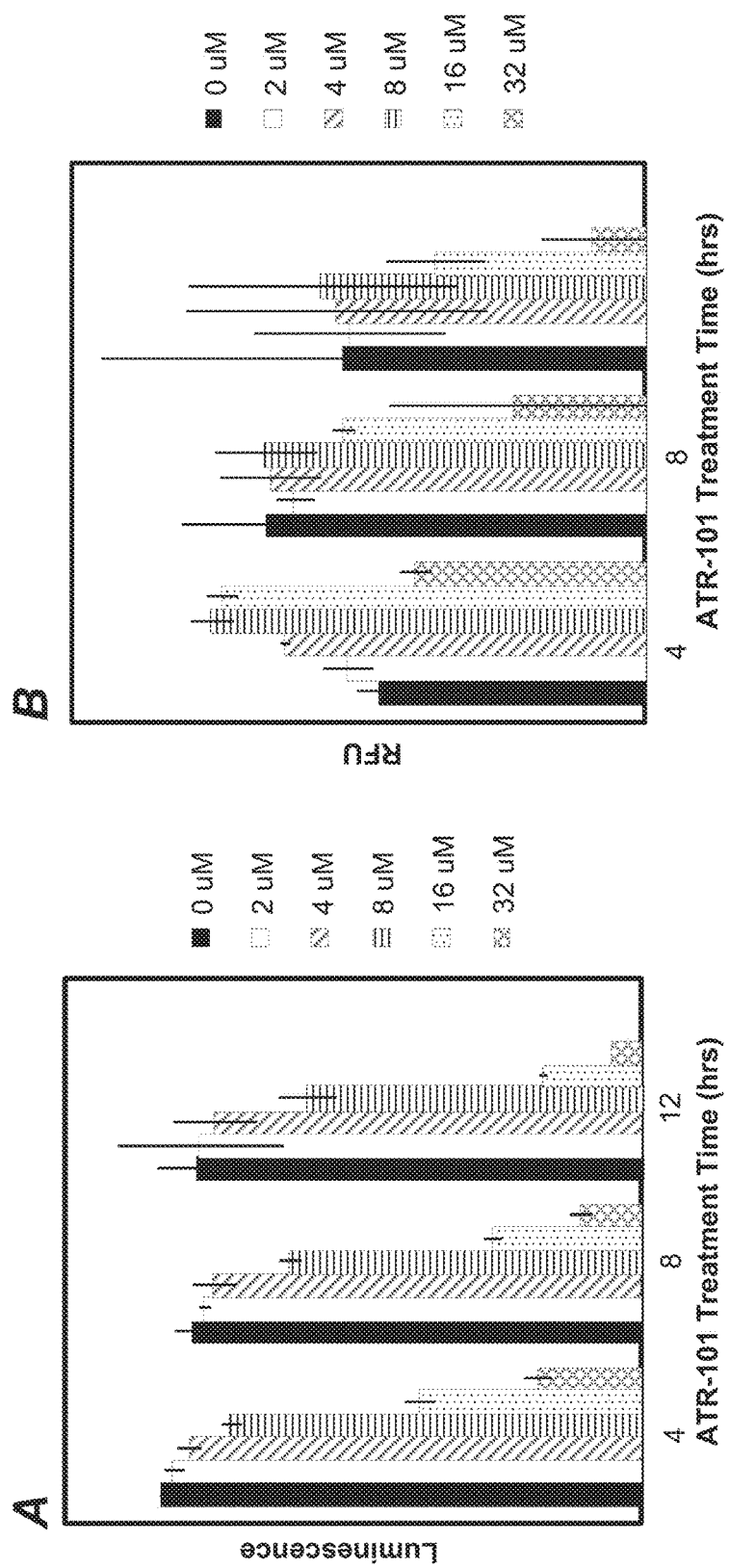
FIG. 11 depicts the effects of ATR-101 on H295R cell (A) ATP levels and (B) on reduction of resazurin. The indicated concentrations of ATR-101 were added to H295R cells (20,000 cells/well for the ATP assay and 40,000 cells/well for the resazurin assay plated the day before in serum-free media). The bars show the mean luminescence and fluorescence intensities of cells treated with the concentrations of ATR-101 indicated to the right of the graphs for the time indicated below the bars.

Cellular reducing activity was determined by measuring resazurin reduction using the PrestoBlue® Cell Viability Reagent (Invitrogen). Addition of up to 8 µM ATR-101 to H295R cells increased the fluorescence signal in a time- and concentration-dependent manner, whereas higher ATR-101 concentrations reduced the fluorescence (FIG. 11B). The opposite effects of different concentrations of ATR-101 on resazurin reducing activity suggest that ATR-101 has multiple effects on cells. Low to moderate concentrations of ATR-101 increased reducing activity, but had little effect on ATP levels. High concentrations of ATR-101 reduced both reducing activity and ATP levels, presumably because of a decrease in cell viability.

To investigate the mechanism whereby ATR-101 kills cells in culture, the effects of cholesterol depletion on the ATP levels of H295R cells cultured in the presence of ATR-101 was investigated. The cells were cultured in the presence of methyl-β-cyclodextrin (MβCD), which can sequester cholesterol and thereby deplete free cholesterol in the cells. The level of ATP in H295R cells was not significantly altered by culture in the presence of 2 mM MβCD (FIG. 12B). Significantly, the ATP levels of cells cultured in the presence of MβCD were unaffected by up to 32 µM ATR-101. MβCD increased the concentration of ATR-101 required for half-maximal depletion of ATP levels more than 4-fold.

To determine if the effect of MβCD on ATR-101 cytotoxicity was due to cholesterol depletion, H295R cells were cultured in the presence of the equivalent amount of MβCD complexed with cholesterol (FIG. 12C). Parallel analysis of these cells demonstrated that MβCD complexed with cholesterol alone reduced the ATP levels of H295R cells. Treatment of the cells with ATR-101 caused a further reduction in the level of ATP in the cells. The protection of H295R cells from the cytotoxicity of ATR-101 by culture in the presence of MβCD was therefore due to cholesterol depletion in these cells.

Figure 12F:
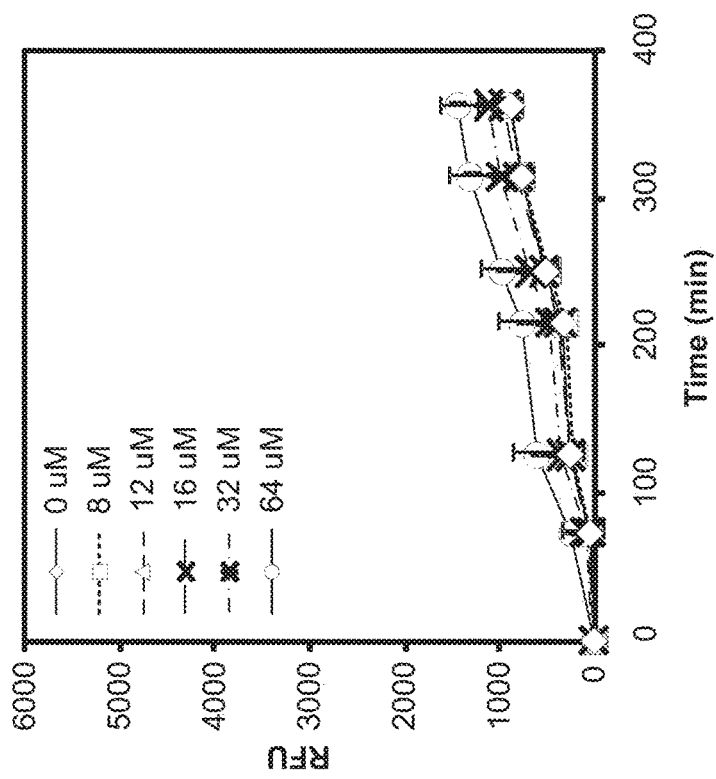
Figure 12E:
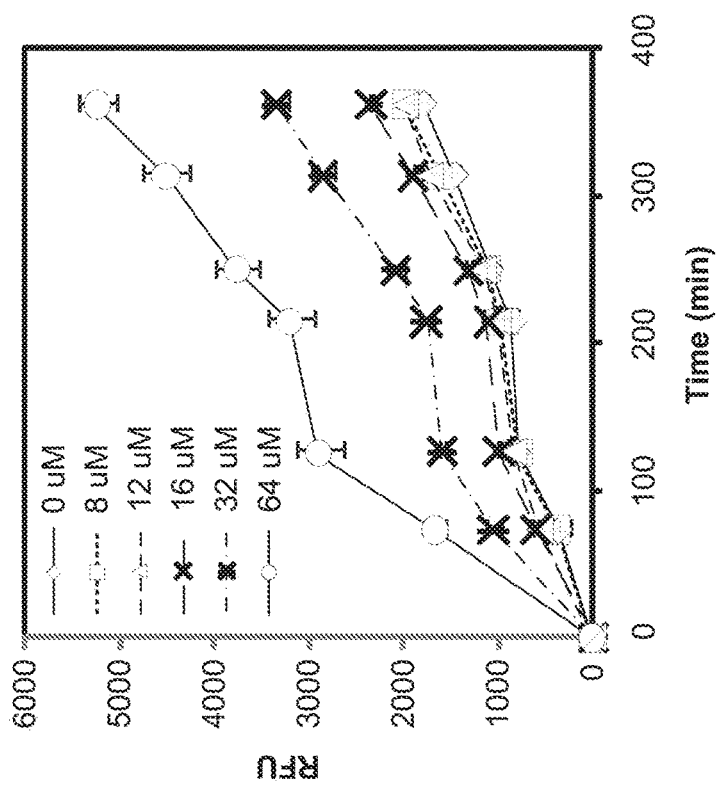

To determine if the culture of H295R cells in the presence of MβCD altered ATR-101 entry into cells, the effects of MβCD on ATR-101 induced changes in reducing activity were examined (FIG. 12D-F). Culture in the presence of MβCD alone had little effect on the reducing activity of the cells (FIG. 12E). MβCD did not suppress the increase in resazurin reducing activity caused by ATR-101. Rather, cells cultured in the presence of MβCD exhibited a larger increase in reducing activity in response to ATR-101, potentially caused by MβCD suppression of ATR-101 cytotoxicity. Cells cultured in the presence of MβCD complexed with cholesterol exhibited lower reducing activities both in the absence and in the presence of ATR-101. The reduction in reducing activity was likely related to the reduction in ATP levels caused by MβCD complexed with cholesterol.

The results indicate that the reduction in ATP levels is not directly related to changes in the reducing activities of the cells, and the mechanism of ATR-101 cytotoxicity is not determined solely by inhibition of respiration even though ATR-101 is known to inhibit complex II of the electron transport chain in isolated mitochondria. In combination, these results demonstrate that MβCD does not prevent the entry of ATR-101 into H295R cells, and that MβCD protection from ATR-101 cytotoxicity is likely due to sequestration of free cholesterol in the cells.

Example 9

Figure 13:
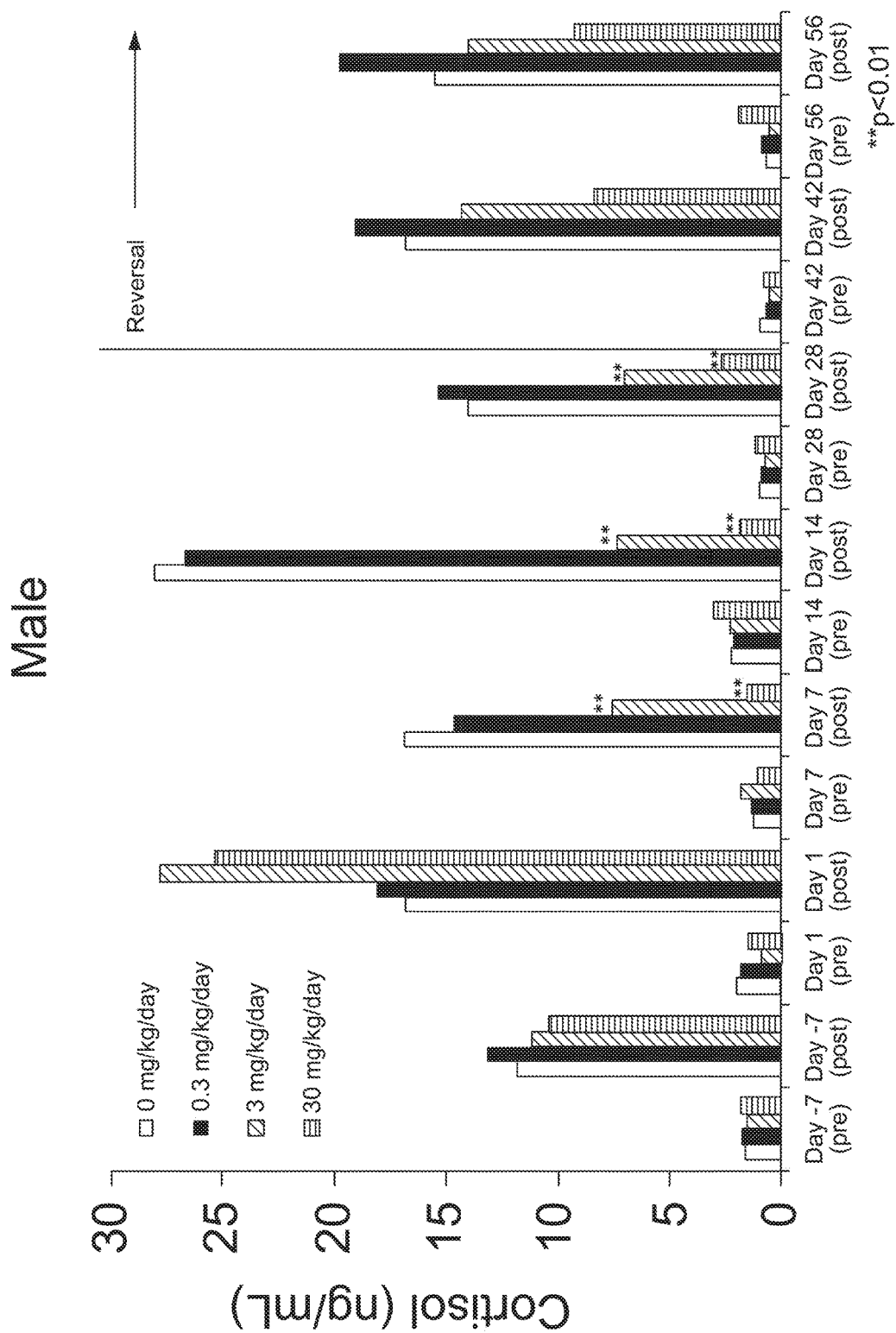
FIG. 13 depicts the basal and ACTH-stimulated cortisol levels in male dogs administered 0, 0.3, 3, or 30 mg/kg/day of ATR-101 measured at 1, 7, 14, and 28 days during treatment and during recovery period.
Figure 14:
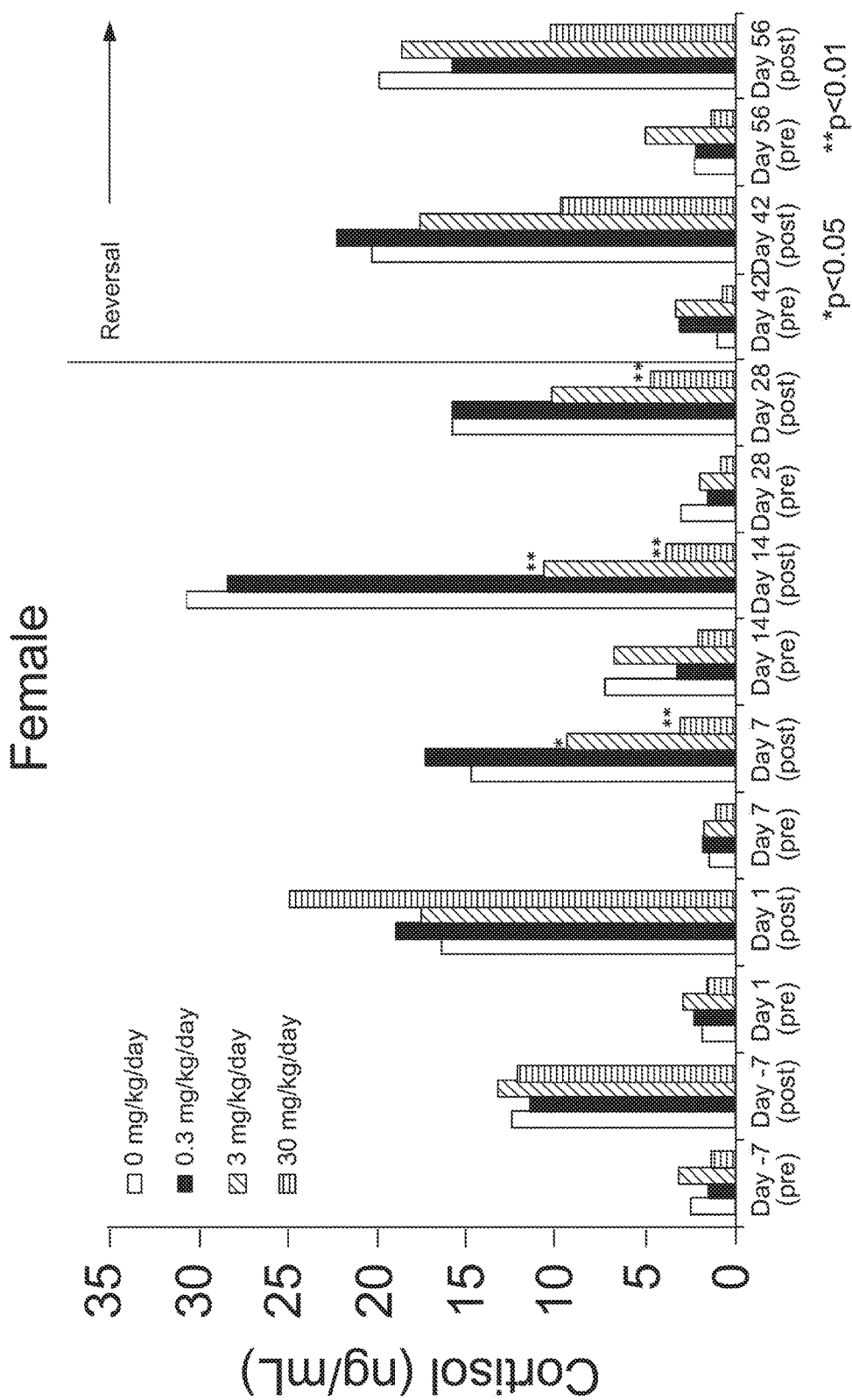
FIG. 14 depicts the basal and ACTH-stimulated cortisol levels in female dogs administered 0, 0.3, 3, or 30 mg/kg/day of ATR-101 measured at 1, 7, 14, and 28 days during treatment and during recovery period.

Basal and adrenocorticotropic hormone (ACTH)-stimulated cortisol levels were measured in dogs at pre-test and 1, 7, 14, and 28 days during ATR-101 treatment at various doses (0 mg/kg/day, 0.3 mg/kg/day, 3 mg/kg/day, and 30 mg/kg/day). 6 dogs/sex/dosage group were studied. After 28 days of treatment, 4 dogs/sex/group were euthanized, while 2 dogs/sex/group/ had a 4-week drug-free recovery period and then were euthanized. Plasma cortisol concentrations (ng/ml) in male and female dogs were determined prior to ACTH stimulation and 0.5 and 1 hour after ACTH stimulation. Marked drug-associated decreases in ACTH responses occurred in ATR-101-treated male and female dogs at 3 mg/kg/day and 30 mg/kg/day beginning day 7 of treatment, continuing through day 14 and day 28 of treatment (FIGS. 13 and 14). At days 42 and 56 during the recovery period, reversal of the cortisol-suppressive effects is observed (FIGS. 13 and 14).

Example 10

Figure 15E:
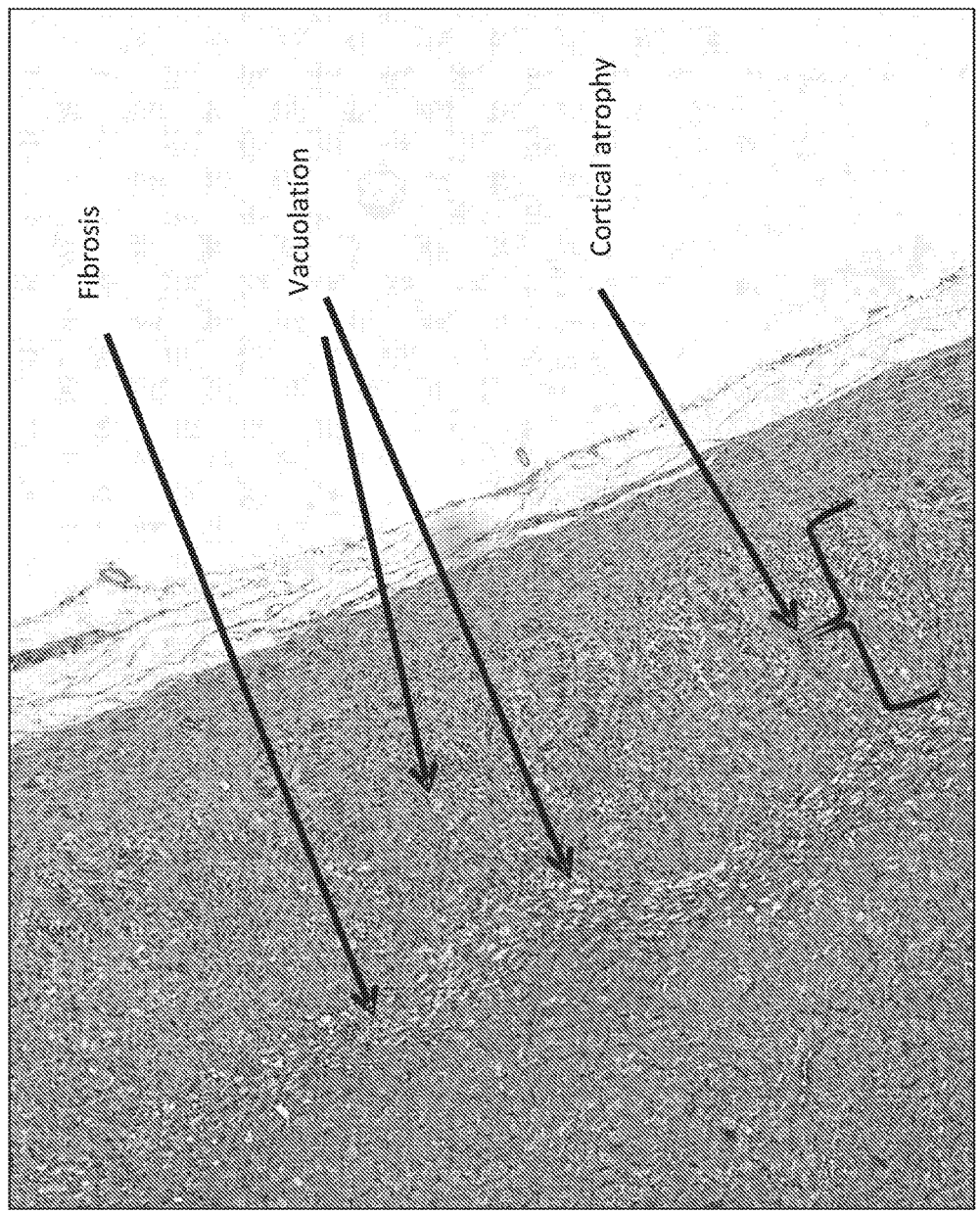

Left and right adrenal glands from dogs treated with a high dose 300 mg/kg/day of ATR-101 for 28 days and control animals were collected at necropsy and fixed in 10% neutral buffered formalin, processed by routine paraffin technique, sectioned longitudinally, and stained with hematoxylin and eosin for routine light microscopy (FIGS. 15A-E). Significant effects were observed in the adrenal gland of dogs treated with ATR-101 at day 28, including fibrosis (deposition of loose to compact fibrovascular tissue within the corticomedullary junction), vacuolation (intracytoplasmic small to medium-sized clear vacuoles within the cytoplasm of the zona fasciculata and zone reticularis of the cortex), and cortical atrophy (decreased thickness of the adrenal cortex due to decreased cell size and numbers of cells comprising the zona fasciculata and zona reticularis) (FIGS. 15D, 15E).

Example 11

Left and right adrenal glands from male and female dogs treated with various doses of ATR-101 (0 mg/kg/day, 0.3 mg/kg/day, 3 mg/kg/day, or 30 mg/kg/day) for 28 days were collected at necropsy and weighed. Dose-related changes in adrenal gland weights occurred in both sexes (FIGS. 16A and 17A). Absolute and relative (adrenal-to-body (Adrenal:BW (%)) and adrenal-to-brain (Adrenal:BrW) weight ratios) adrenal weights were decreased 14% to 55% in both sexes at ≥3 mg/kg/day (FIGS. 16A-C and 17A-C). After the 4 week recovery period, adrenal weights remained decreased 6% to 11% in males at 3 mg/kg/day and 10% to 32% in both sexes at 30 mg/kg/day. Adrenal weight changes were associated with histologic changes including adrenal cortical atrophy, fibrosis, and vacuolation in both sexes at ≥3 mg/kg/day as described in Example 10 (FIGS. 15A-E). Histologic changes in the adrenal glands persisted after the recovery period.

Example 12

Figure 18:
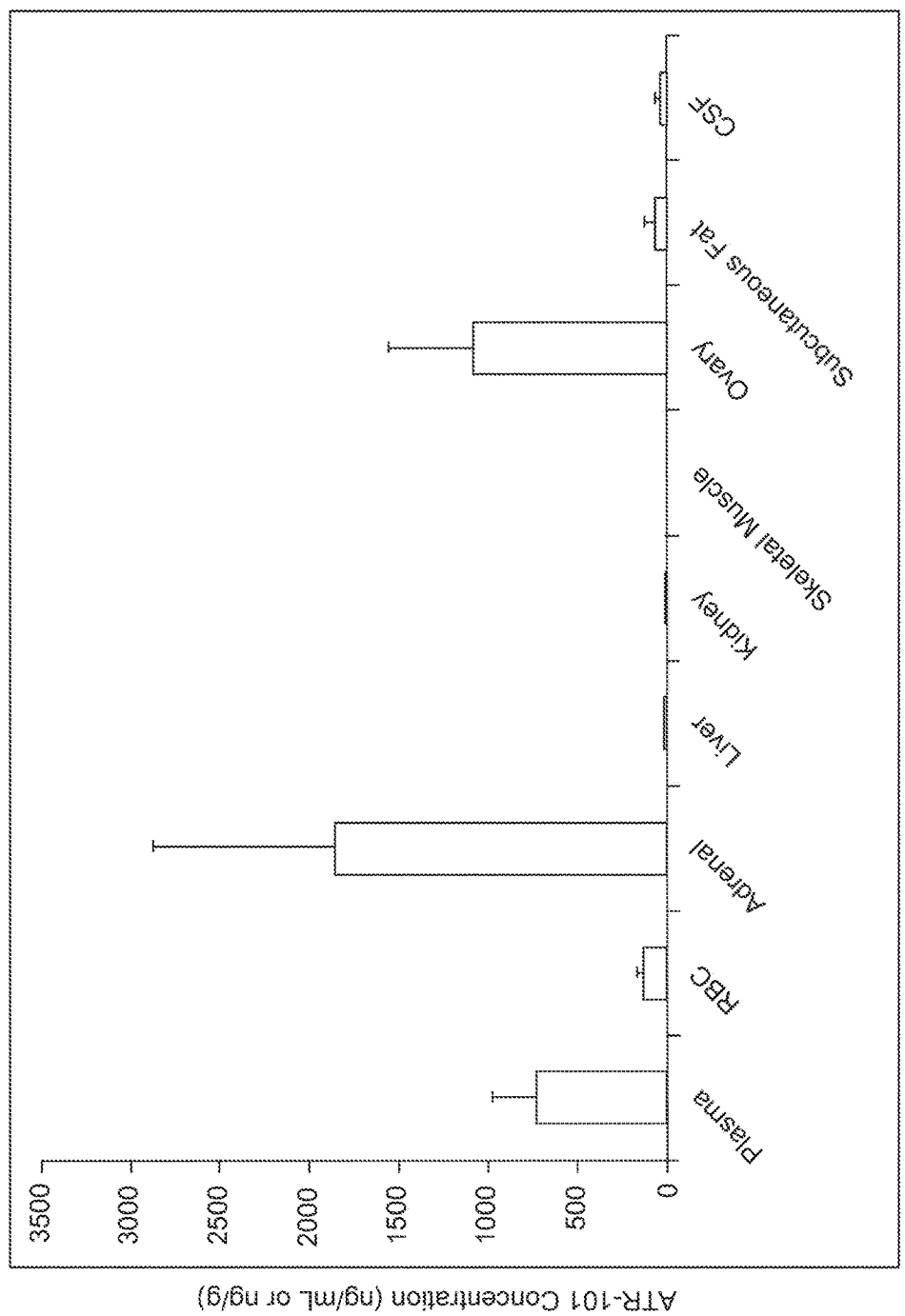
FIG. 18 depicts tissue distribution of ATR-101 in female rats given 100 mg/kg/day for 7 days. Values shown are mean±standard deviation, N=3.
Figure 19:
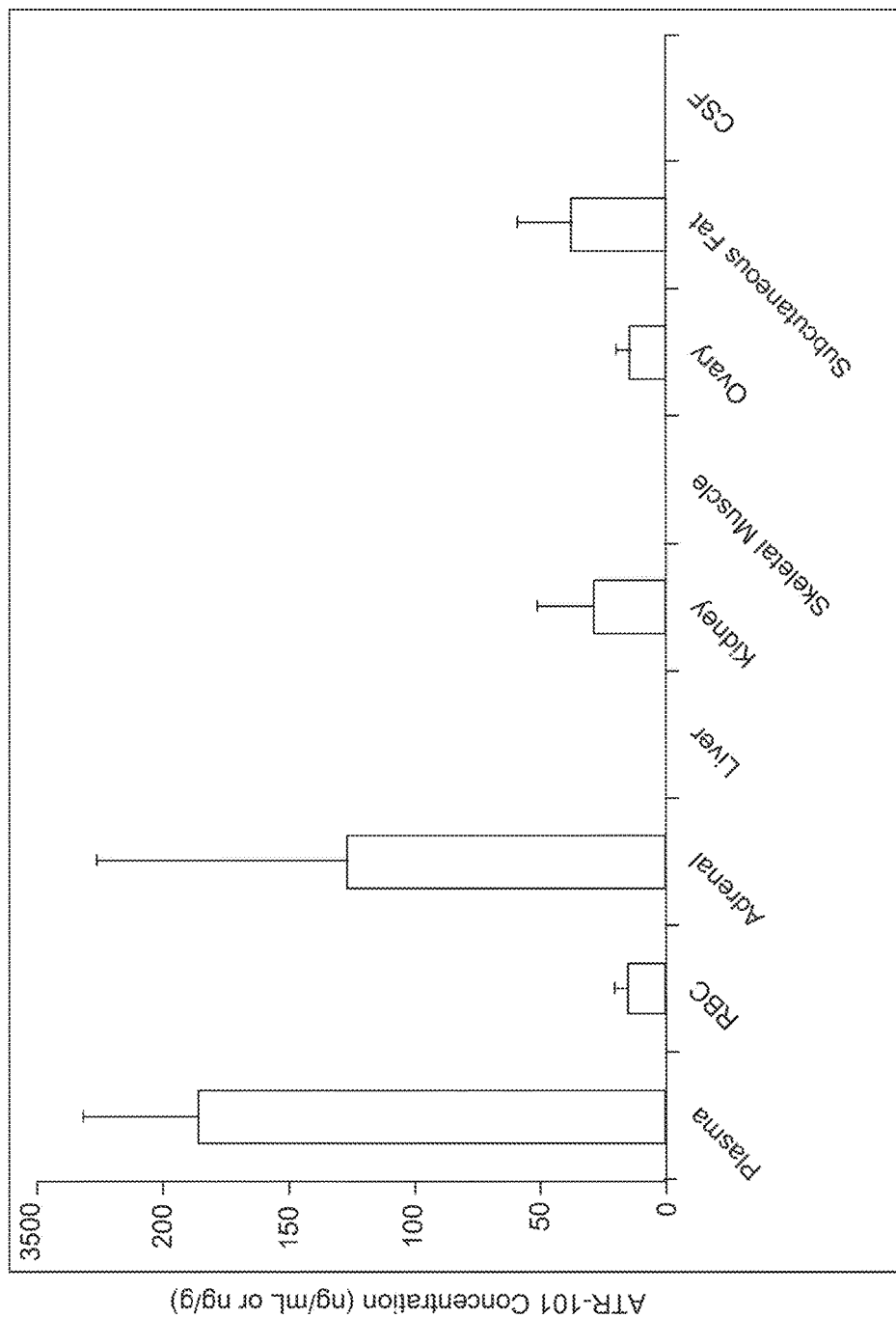
FIG. 19 depicts tissue distribution of ATR-101 in female dogs given 3 mg/kg/day for 7 days. Values shown are mean±standard deviation, N=3.
Figure 20:
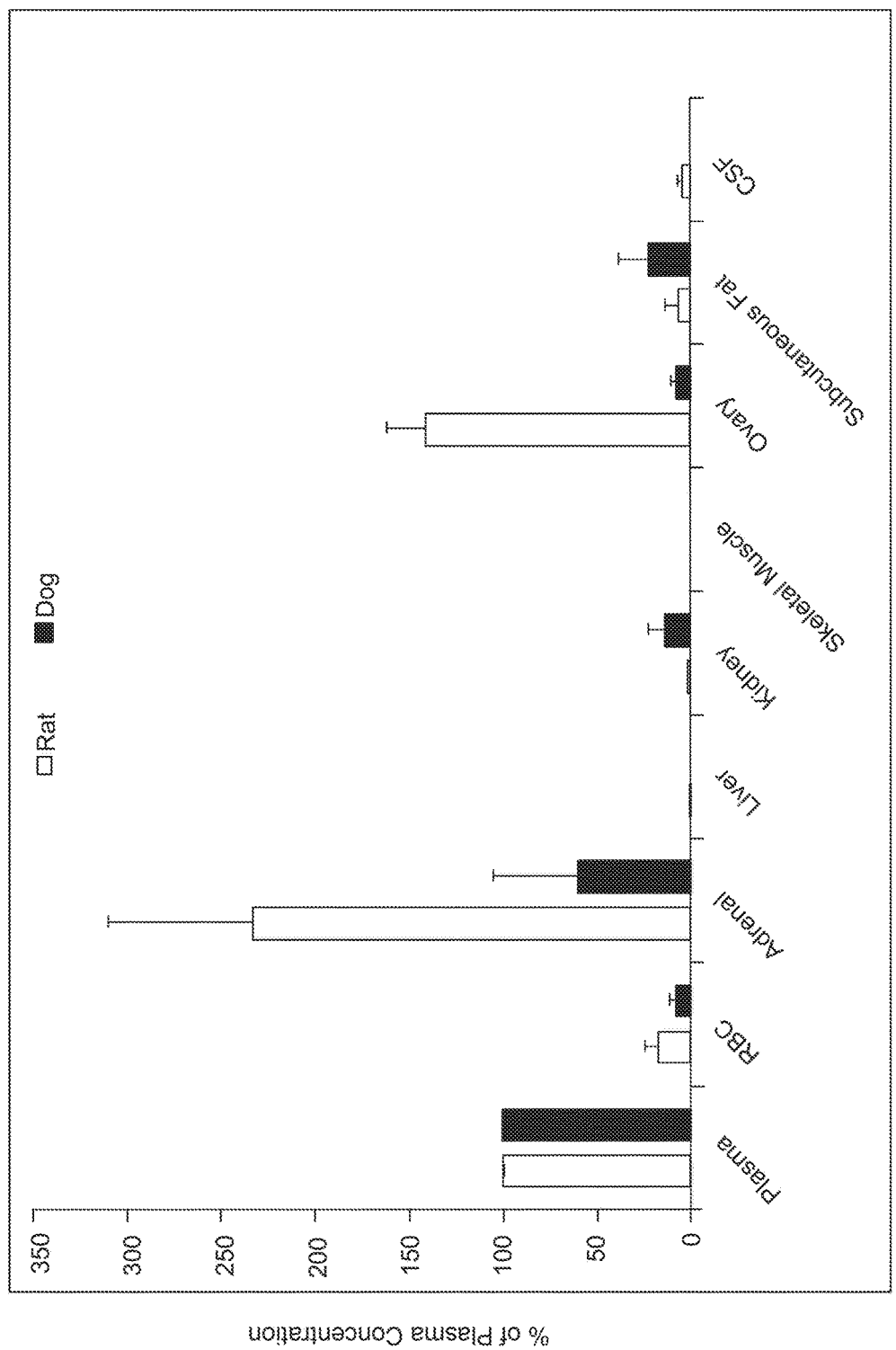
FIG. 20 depicts tissue distribution of ATR-101 in rats and dogs as a percentage of plasma concentration. Values shown are mean±standard deviation, N=3.

Tissue distribution of ATR-101 in 3 rats and 3 dogs was examined. ATR-101 concentrations were measured in plasma, red blood cells, adrenal gland, liver, kidney, skeletal muscle, ovary, subcutaneous fat, and cerebral spinal fluid. FIG. 18 shows tissue distribution of ATR-101 in female rats (ng/mL or ng/g) administered 100 mg/kg/day for 7 days. ATR-101 concentrations in rats were higher in adrenal gland (~2×) and ovary (~1.4×) than in plasma. FIG. 19 shows tissue distribution of ATR-101 in female dogs (ng/mL or ng/g) administered 3 mg/kg/day for 7 days. ATR-101 concentrations in dogs were similar in adrenal gland and plasma. ATR-101 concentrations in the adrenal glands of rats and dogs do not correspond with the relative sensitivities of these species to adrenal toxicity, suggesting that tissue accumulation alone does not explain the adrenolytic mechanism(s) of action. FIG. 20 shows tissue distribution of ATR-101 in rats and dogs as a percentage of plasma concentration. ATR-101 does not appear to cross the blood-brain barrier in either species. Low levels of ATR-101 that were observed in the cerebral spinal fluid (CSF) of rats were likely caused by contamination of CSF with blood.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Veronica Burns and Yunhui Cheng are thanked for their work on the experiments in H295R cells and xenografts, performed under the direct supervision of Tom Kerppola.

All embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for treating a patient diagnosed as having 21-hydroxylase deficient congenital adrenal hyperplasia comprising administering to the patient a therapeutically effective amount of N-(2,6-bis(1-methylethyl)phenyl)-N'-((1-(4-(dimethylamino)phenyl)cyclopentyl)-methyl)urea hydrochloride (ATR-101), wherein ATR-101 is administered orally one, two, three or four time daily to the patient.

* * * * *

UNITED STATES PATENT AND TRADEMARK OFFICE
CERTIFICATE OF CORRECTION

PATENT NO. : 9,877,937 B2
APPLICATION NO. : 15/170682
DATED : January 30, 2018
INVENTOR(S) : Gary Hammer et al.

It is certified that error appears in the above-identified patent and that said Letters Patent is hereby corrected as shown below:

On the Title Page

Item (73), Assignees:
"The Regents of the Univeristy of Michigan" should read, --The Regents of the University of Michigan--.

Item (57), Abstract, Line 6:
"N-(2,6-bis(1-methylethyl)phenyl)-N'-((1-(4-(dimethyl amino)phenyl)cyclopentyl)-methyl)urea hydrochloride" should read, --N-(2,6-bis(1-methylethyl)phenyl)-N'-((1-(4-(dimethylamino)phenyl)cyclopentyl)-methyl)urea hydrochloride--.

Page 2, Column 1, Item (56), References Cited, Other Publications, Line 6:
"Villa et al., "Modulation of cytotoxic drug activity by mitotane and Ionidamine in human adrenocortical carcinoma cells," *International Journal of Oncology, 14(1)*: 133-138 (1999)." should read, --Villa et al., "Modulation of cytotoxic drug activity by mitotane and lonidamine in human adrenocortical carcinoma cells," *International Journal of Oncology 14*(1): 133-138 (1999).--.

Page 2, Column 1, Item (56), References Cited, Other Publications, Line 28:
"Krause et al., "Divergent Pharmacologic Activitites of PD 132301-2 and CL 277,082, Urea Inhibitors of Acyl-CoA: Cholesterol Acyltransferase," *The Journal of Pharmacology and Experimental Therapeutics* 267(2): 734-743, 1993." should read, --Krause et al., "Divergent Pharmacologic Activities of PD 132301-2 and CL 277,082, Urea Inhibitors of Acyl-CoA: Cholesterol Acyltransferase," *The Journal of Pharmacology and Experimental Therapeutics 267*(2):734-743, 1993.--.

Page 2, Column 2, Item (56), References Cited, Other Publications, Line 12:
"Merke et al., "Congential adrenal hyperplasia," *Lancet*, 365: 2125-2136, Jun. 18, 2005." should read, --Merke et al., "Congenital adrenal hyperplasia," *Lancet 365*:2125-2136, Jun. 18, 2005.--.

Signed and Sealed this
Twenty-sixth Day of June, 2018

Andrei Iancu
*Director of the United States Patent and Trademark Office*

CERTIFICATE OF CORRECTION (continued)
U.S. Pat. No. 9,877,937 B2

Page 2, Column 2, Item (56), References Cited, Other Publications, Line 14:
"Purchase et al., "Inhibitors of Acyl-CoA:Cholesterol Acyltransferase: Novel Trisbustituted Ureas as Hypocholesterolemic Agents," *Bioorganic & Medicinal Chemistry* 5(4): 739-747, 1997." should read, --Purchase et al., "Inhibitors of Acyl-CoA:Cholesterol Acyltransferase: Novel Trisubstituted Ureas as Hypocholesterolemic Agents," *Bioorganic & Medicinal Chemistry* 5(4):739-747, 1997.--.

Page 2, Column 2, Item (56), References Cited, Other Publications, Line 55:
"Wolfgang et al., "Hepatic and Adrenal Toxicity of a Novel Lipid Regulator in Beagle Dogs," *Fundemantal and Applied Toxicology* 26: 272-281, 1995." should read, --Wolfgang et al., "Hepatic and Adrenal Toxicity of a Novel Lipid Regulator in Beagle Dogs," *Fundamental and Applied Toxicology* 26:272-281, 1995.--.

In the Claims

Column 28, Lines 51-52:
"wherein ATR-101 is administered orally one, two, three or four time daily to the patient." should read, --wherein ATR-101 is administered orally one, two, three or four times daily to the patient.--.